(12) United States Patent
Vondrell et al.

(10) Patent No.: US 11,046,428 B2
(45) Date of Patent: Jun. 29, 2021

(54) TILTROTOR PROPULSION SYSTEM FOR AN AIRCRAFT

(71) Applicant: General Electric Company, Schenectady, NY (US)

(72) Inventors: Randy M. Vondrell, Cincinnati, OH (US); Matthew Ryan Polakowski, West Chester, OH (US); Kurt David Murrow, Liberty Township, OH (US); Glenn Crabtree, Oregonia, OH (US); Darek Tomasz Zatorski, Fort Wright, KY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 16/502,913

(22) Filed: Jul. 3, 2019

(65) Prior Publication Data

US 2020/0085988 A1    Mar. 19, 2020

Related U.S. Application Data

(63) Continuation of application No. 15/259,654, filed on Sep. 8, 2016, now Pat. No. 10,384,774.

(51) Int. Cl.
*B64C 29/00* (2006.01)
*B64C 27/28* (2006.01)
(Continued)

(52) U.S. Cl.
CPC .......... *B64C 29/0033* (2013.01); *A61L 9/122* (2013.01); *B64C 21/06* (2013.01);
(Continued)

(58) Field of Classification Search
CPC ..... B64D 27/24; B64C 29/0033; B64C 27/08; B64C 27/05; B64C 27/28; B64C 29/0075; B64C 27/22
See application file for complete search history.

(56) References Cited

U.S. PATENT DOCUMENTS

| | | |
|---|---|---|
| 3,089,666 A | 5/1963 | Quenzler |
| 3,141,633 A | 7/1964 | MacKay |

(Continued)

FOREIGN PATENT DOCUMENTS

| | | |
|---|---|---|
| DE | 102014000509 A1 | 7/2015 |
| WO | WO2015/143093 A2 | 9/2015 |

OTHER PUBLICATIONS

Wikipedia, NASA GL-10 Greased Lightning, https://en.wikipedia.org/wiki/NASA_GL-10_Greased_Lightning.

(Continued)

*Primary Examiner* — Richard R. Green
*Assistant Examiner* — Michael B. Kreiner
(74) *Attorney, Agent, or Firm* — Dority & Manning, P.A.

(57) ABSTRACT

A method for operating a propulsion system of an aircraft includes moving a plurality of forward and aft propulsors to a vertical thrust position. While in the vertical thrust positions, the method also includes providing a first forward to aft ratio of electric power to the plurality of forward and aft propulsors. The method also includes moving the plurality of forward and aft propulsors to a forward thrust position. While in the forward thrust positions, the method also includes providing a second forward to aft ratio of electric power to the plurality of forward and aft propulsors. The first forward to aft ratio of electric power is different than the second forward to aft ratio of electric power to provide certain efficiencies for the aircraft.

20 Claims, 15 Drawing Sheets

(51) Int. Cl.
*H02J 50/10* (2016.01)
*A61L 9/12* (2006.01)
*H02J 7/00* (2006.01)
*H02J 7/02* (2016.01)
*B64C 21/06* (2006.01)
*B64D 27/14* (2006.01)
*B64D 27/24* (2006.01)
*H02P 9/04* (2006.01)
*B64C 3/38* (2006.01)
*B64D 27/02* (2006.01)

(52) U.S. Cl.
CPC .............. *B64C 27/28* (2013.01); *B64C 29/00* (2013.01); *B64D 27/14* (2013.01); *B64D 27/24* (2013.01); *H02J 7/0042* (2013.01); *H02J 7/025* (2013.01); *H02J 50/10* (2016.02); *H02P 9/04* (2013.01); *A61L 2209/133* (2013.01); *B64C 3/385* (2013.01); *B64C 29/0008* (2013.01); *B64D 2027/026* (2013.01); *B64D 2221/00* (2013.01); *Y02T 50/60* (2013.01)

(56) References Cited

U.S. PATENT DOCUMENTS

| | | | |
|---|---|---|---|
| 3,181,810 A | 5/1965 | Olson | |
| 3,360,217 A | 12/1967 | Trotter | |
| 4,925,131 A | 5/1990 | Eickmann | |
| 4,982,914 A | 1/1991 | Eickmann | |
| 5,419,514 A | 5/1995 | Ducan | |
| 5,823,468 A | 10/1998 | Bothe | |
| 6,138,943 A | 10/2000 | Huang | |
| 6,655,631 B2 | 12/2003 | Austen-Brown | |
| 6,892,980 B2 | 5/2005 | Kawai | |
| 7,188,802 B2 | 3/2007 | Magre | |
| 7,472,863 B2 | 1/2009 | Pak | |
| 7,874,513 B1 | 1/2011 | Smith | |
| 8,544,787 B2 | 10/2013 | Lee et al. | |
| 8,616,492 B2 | 12/2013 | Oliver | |
| 8,640,985 B2 | 2/2014 | Brunken, Jr. | |
| 8,655,510 B2 | 2/2014 | Eglin | |
| 8,708,273 B2 | 4/2014 | Oliver | |
| 8,720,814 B2 | 5/2014 | Smith | |
| 8,727,271 B2 | 5/2014 | Salyer | |
| 8,733,690 B2 | 5/2014 | Bevirt et al. | |
| 8,777,150 B2 | 7/2014 | Wang | |
| 8,800,912 B2 | 8/2014 | Oliver | |
| 8,870,114 B2 | 10/2014 | Botti et al. | |
| 8,907,595 B2 | 12/2014 | Weibel et al. | |
| 8,915,464 B2 | 12/2014 | Ferrier et al. | |
| 8,931,732 B2 | 1/2015 | Sirohi et al. | |
| 9,008,942 B2 | 4/2015 | Dyrla et al. | |
| 9,045,226 B2 | 6/2015 | Piasecki et al. | |
| 9,126,678 B2 | 9/2015 | Ross et al. | |
| 9,162,771 B2 | 10/2015 | Roggemans et al. | |
| 9,174,728 B2 | 11/2015 | Altmikus et al. | |
| 9,187,174 B2 | 11/2015 | Shaw | |
| 9,199,732 B2 | 12/2015 | Isaac et al. | |
| 9,242,729 B1 | 1/2016 | Wang et al. | |
| 9,248,908 B1 | 2/2016 | Luyks | |
| 9,284,059 B2 | 3/2016 | Prud Homme-Lacroix | |
| 9,475,579 B2 | 10/2016 | Fredericks et al. | |
| 9,493,235 B2 | 11/2016 | Zhou et al. | |
| 9,694,908 B2 | 7/2017 | Razroev | |
| 9,701,406 B2 | 7/2017 | Robertson et al. | |
| 9,896,200 B2 | 2/2018 | Fredericks et al. | |
| 2005/0230519 A1 | 10/2005 | Hurley | |
| 2015/0266571 A1 | 9/2015 | Bevirt et al. | |
| 2015/0284075 A1 | 10/2015 | Alber | |
| 2015/0360775 A1 | 12/2015 | Arai | |
| 2015/0380999 A1 | 12/2015 | Joshi et al. | |
| 2016/0207625 A1 | 7/2016 | Judas et al. | |
| 2016/0229531 A1 | 8/2016 | Robertson et al. | |
| 2016/0244158 A1 | 8/2016 | Fredericks et al. | |
| 2016/0288903 A1 | 10/2016 | Rothhaar et al. | |
| 2016/0304194 A1 | 10/2016 | Bevirt et al. | |
| 2016/0325629 A1 | 11/2016 | Siegel et al. | |
| 2017/0029131 A1 | 2/2017 | Steinwandel et al. | |
| 2017/0210469 A1 | 7/2017 | Piasecki et al. | |
| 2017/0349293 A1 | 12/2017 | Klemen et al. | |
| 2018/0002011 A1 | 1/2018 | McCullough et al. | |
| 2018/0002012 A1 | 1/2018 | McCullough et al. | |
| 2018/0002026 A1 | 1/2018 | Oldroyd et al. | |
| 2018/0037332 A1 | 2/2018 | Hughes et al. | |
| 2018/0044012 A1 | 2/2018 | Groninga et al. | |
| 2018/0044013 A1 | 2/2018 | Groninga et al. | |
| 2018/0057157 A1 | 3/2018 | Groninga et al. | |

OTHER PUBLICATIONS

International Search Report Corresponding to Application No. PCT/US2017/046185 dated Dec. 15, 2017.

TILTROTOR PROPULSION SYSTEM FOR AN AIRCRAFT

CROSS-REFERENCE TO RELATED APPLICATIONS

This application is a continuation application of U.S. application Ser. No. 15/259,654, filed Sep. 8, 2016, which is hereby incorporated by reference in its entirety.

FIELD OF THE INVENTION

The present subject matter relates generally a propulsion system for an aircraft having a plurality of tilt rotors, and an aircraft including the same.

BACKGROUND OF THE INVENTION

Aircraft have been developed with a capability for performing vertical takeoff and landings. Such a capability may allow for the aircraft to reach relatively rugged terrains and remote locations, where it may be impractical or infeasible to construct a runway large enough to allow for a traditional aircraft (lacking vertical takeoff capability) to takeoff or land.

Typically these aircraft capable of performing vertical takeoff and landings have engines that are vectored to generate both vertical thrust and forward thrust. However, an amount of thrust necessary to takeoff and land vertically may not be equal to an amount of thrust required for the aircraft to maintain forward flight. Accordingly, existing aircraft capable of performing vertical takeoff and landing include engines that may be well suited for generating vertical thrust, but that may not be very well suited for efficient forward flight. Therefore, an aircraft capable of performing a vertical takeoff and landing, in addition to achieving more efficient forward flight would be useful.

BRIEF DESCRIPTION OF THE INVENTION

Aspects and advantages of the invention will be set forth in part in the following description, or may be obvious from the description, or may be learned through practice of the invention.

In one exemplary aspect of the present disclosure, a method of operating a propulsion system of an aircraft is provided. The aircraft includes a plurality of forward propulsors and a plurality of aft propulsors, each powered by an electric power source and rotatable between a forward thrust position and a vertical thrust position. The method includes moving the plurality of forward propulsors and the plurality of aft propulsors to the vertical thrust positions, and providing a first forward to aft ratio of electric power to the plurality of forward propulsors and the plurality of aft propulsors from the electric power source, such that the plurality of forward propulsors and plurality of aft propulsors each generate vertical thrust. The method also includes moving the plurality of forward propulsors and the plurality of aft propulsors to the forward thrust positions, and providing a second forward to aft ratio of electric power to the plurality of forward propulsors and the plurality of aft propulsors from the electric power source. The first forward to aft ratio of electric power is different than the second forward to aft ratio of electric power.

In another aspect of the present disclosure, a method of operating a propulsion system of an aircraft is provided. The aircraft includes a plurality of primary thrust propulsors and a plurality of secondary thrust propulsors, each powered by an electric power source and rotatable between a forward thrust position and a vertical thrust position. The method includes moving the plurality of primary thrust propulsors to the vertical thrust positions, and providing power to the plurality of primary thrust propulsors to generate a vertical thrust for vertically oriented flight and simultaneously providing a first amount of electrical power to the plurality of secondary thrust propulsors. The method also includes moving the plurality of primary thrust propulsors to the forward thrust positions, and providing a second amount of electrical power to the plurality of secondary thrust propulsors to generate a forward thrust for horizontally oriented flight. The second amount of electrical power is greater than the first amount of electrical power.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which.

DETAILED DESCRIPTION OF THE INVENTION

Figure 1:
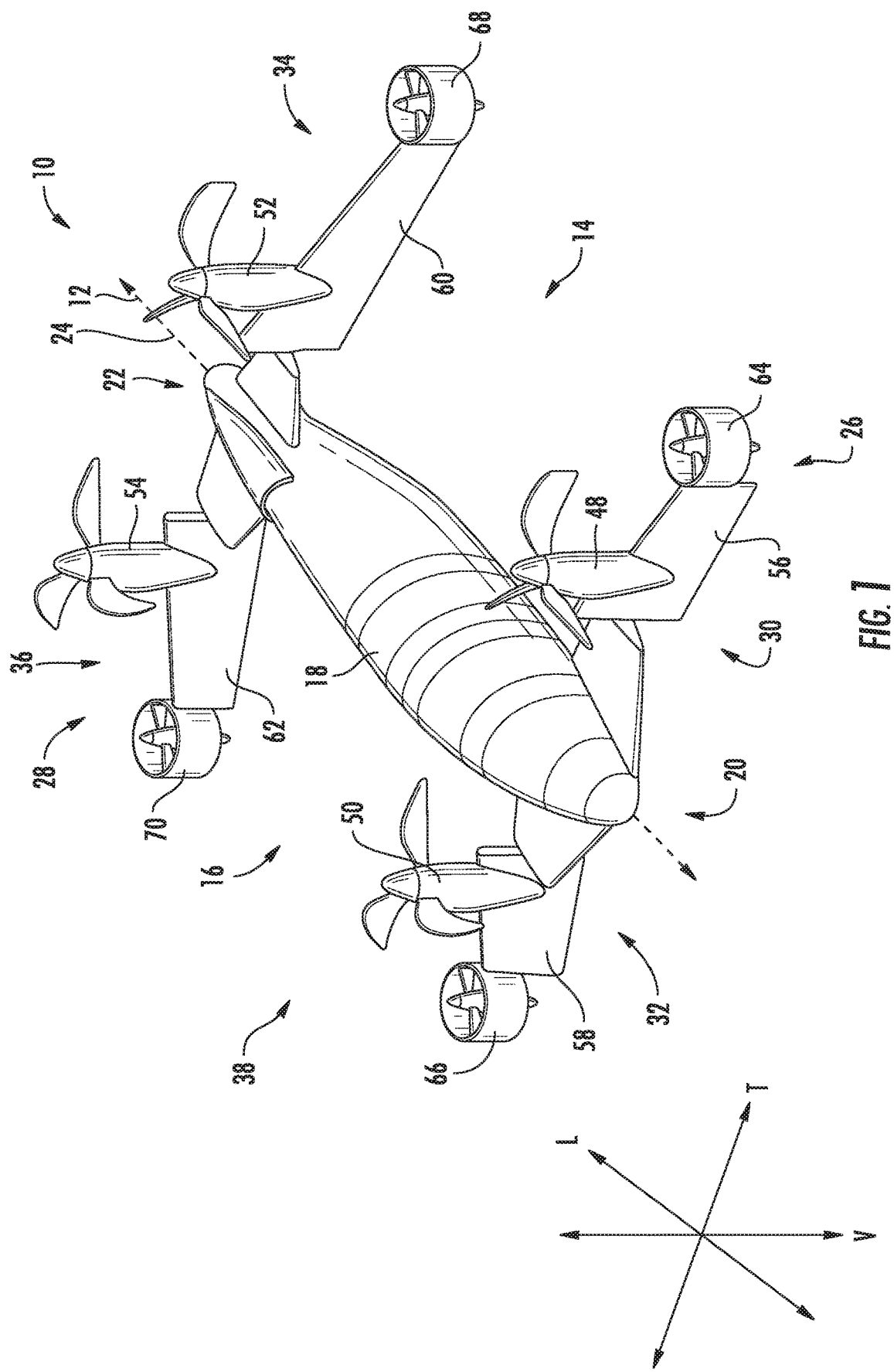
FIG. 1 is a perspective view of an aircraft according to various exemplary embodiments of the present disclosure.

Reference will now be made in detail to present embodiments of the invention, one or more examples of which are illustrated in the accompanying drawings. The detailed description uses numerical and letter designations to refer to features in the drawings. Like or similar designations in the drawings and description have been used to refer to like or similar parts of the invention. As used herein, the terms "first", "second", and "third" may be used interchangeably to distinguish one component from another and are not intended to signify location or importance of the individual components. The terms "forward" and "aft" refer to relative positions along an aircraft, with forward referring to a position closer to a nose section of the aircraft and aft referring to a position closer to a tail section of the aircraft. The terms "port" and "starboard" refer to sides of the aircraft, with port referring to a side of the aircraft that is to the left when facing forward and starboard referring to a side of the aircraft that is to the right when facing forward.

The present application is directed generally towards a method of operating an aircraft having a plurality of tilt rotors enabling vertical takeoff and landing. More specifically, the method of the present disclosure generally includes moving a plurality of forward and aft propulsors to vertical thrust positions and providing a first forward to aft ratio of electric power to the plurality of forward and aft propulsors. Each of the plurality of forward and aft propulsors generate a vertical thrust for the aircraft when the first forward to aft ratio of electric power is provided. The method also includes moving the plurality of forward and aft propulsors to a forward thrust position. While the propulsors are in the forward thrust positions, the method includes providing a second forward to aft ratio of electric power to the plurality of forward and aft propulsors. The first forward to aft ratio of electric power is different than the second forward to aft ratio of electric power to provide certain efficiencies, as discussed in greater detail below.

Figure 2:
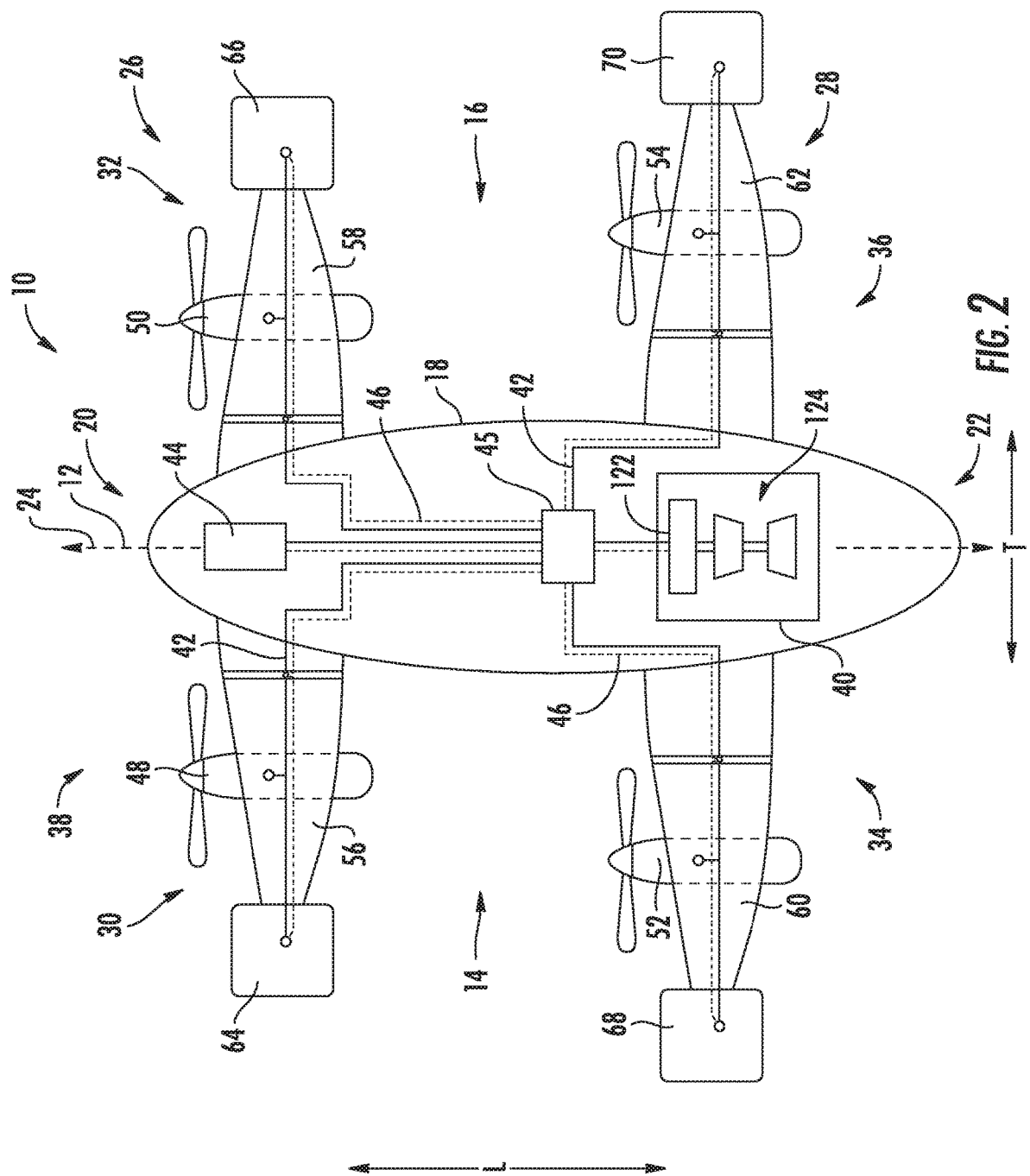
FIG. 2 is a top, schematic of the exemplary aircraft of FIG. 1.

Referring now to the drawings, wherein identical numerals indicate the same elements throughout the figures, FIG. 1 provides a perspective view of an exemplary aircraft 10 as may incorporate various embodiments of the present invention. FIG. 2 provides a top, schematic view of the exemplary aircraft 10 of FIG. 1. As shown in FIGS. 1 and 2 collectively, the aircraft 10 defines a longitudinal direction L (and a longitudinal centerline 12 that extends therethrough), a vertical direction V, and a transverse direction T. Additionally, the aircraft 10 defines a port side 14 and an opposite starboard side 16.

The aircraft 10 includes a fuselage 18 extending between a forward end 20 and an aft end 22 generally along the longitudinal centerline 12 of the aircraft 10, and defining a mean line 24 extending between the forward end 20 and aft end 22 of the fuselage 18 of the aircraft 10. As used herein, the term "fuselage" generally includes all of the body of the aircraft 10, such as an empennage of the aircraft 10. Additionally, as used herein, the "mean line" refers to a midpoint line extending along a length of the fuselage 18, not taking into account the appendages of the aircraft 10 (such as the wing assemblies, discussed below, or any stabilizers).

The aircraft 10 additionally includes a wing assembly attached to or formed integrally with the fuselage 18. Specifically for the embodiment depicted, the aircraft 10 includes a forward wing assembly 26 attached to or formed integrally with fuselage 18 proximate the forward end 20 of the fuselage 18 and an aft wing assembly 28 attached to or formed integrally with the fuselage 18 proximate the aft end 22 of the fuselage 18. Notably, for the embodiment depicted, the forward and aft wing assemblies 26, 28 are each configured as two separate wing sections or sides. Specifically, the forward wing assembly 26 includes a port side 30 and a starboard side 32 and the aft wing assembly 28 similarly includes a port side 34 and an starboard side 36. The port and starboard sides 30, 32 of the forward wing assembly 26 are each separately attached to the fuselage 18 approximately at the same location along the longitudinal centerline 12. Similarly, the port and starboard sides 34, 36 of the aft wing assembly 28 are also each separately attached to the fuselage 18 approximately at the same location along the longitudinal centerline 12. It should be appreciated, however, that in other embodiments, one or both of the forward wing assembly 26 or aft wing assembly 28 may be formed integrally with the fuselage 18 and/or may be formed of a single, continuous section.

Although not depicted, in other embodiments, the aircraft 10 may additionally include one or more stabilizers, such as one or more vertical stabilizers, horizontal stabilizers, etc. Moreover, it will be appreciated, that although not depicted, in certain embodiments, one or more of the forward wing assembly 26 or aft wing assembly 28 may additionally include flaps, such as leading-edge flaps or trailing edge flaps, for assisting with controlling the aircraft 10 during flight.

Referring still to FIGS. 1 and 2, the exemplary aircraft 10 further includes a hybrid-electric propulsion system 38 for providing the aircraft 10 with a desired amount of thrust during operation. Broadly speaking, the exemplary propulsion system 38 includes a port propulsor and a starboard propulsor attached to a wing assembly on opposing sides of the fuselage 18, an electric power source 40 located remotely from the port propulsor and the starboard propulsor, and a primary electric communication bus 42 for electrically connecting the electric power source 40 to the propulsors. Additionally, the primary electric communication bus 42 is operable with a controller 45 for distributing electrical power to the various propulsors through the primary electric communication bus 42. Notably, for the embodiment depicted, the propulsion system 38 additionally includes one or more energy storage devices 44 (such as one or more batteries) and a secondary electric communication bus 46. The one or more energy storage devices 44 are electrically connected to the primary and secondary electric communication buses 40, 46. Additionally, the secondary electric communication bus 46 is provided for redundancy purposes, and each of the propulsors are additionally electrically connected to the electric power source 40 through the secondary electric communication bus 46.

Specifically for the embodiment depicted, the propulsion system 38 includes a port forward propulsor and a starboard forward propulsor attached to the forward wing assembly 26 on opposing sides of the fuselage 18, as well as a port aft propulsor and a starboard aft propulsor similarly attached to the aft wing assembly 28 on opposing sides of the fuselage 18. As will be discussed in greater detail below, each of these propulsors are configured as relatively high diameter, principal thrust fans ("PT fans"). Accordingly, the port forward propulsor is a port forward PT fan 48, the starboard forward propulsor is a starboard forward PT fan 50, the port aft propulsor is a port aft PT fan 52, and the starboard aft propulsor is a starboard aft PT fan 54. Each of the port forward PT fan 48, starboard forward PT fan 50, port aft PT fan 52, and starboard aft PT fan 54 are in electrical communication with the electric power source 40, via the primary electric communication bus 42, such that each of the propulsors are powered by the electric power source 40. It should be appreciated, that although the variety of propulsors are described herein as "fans", the term is not intended to limit the present disclosure to any single type of electric propulsor. Unless specifically limited by the claims, in other embodiments of the present disclosure, any propulsors described as a "fan" herein may additionally, or alternatively, be configured as any other suitable propulsion device, including, without limitation, ducted fans, un-ducted fans, single stage fans (i.e., fans having a single stage of propellers), and multiple counter-rotating stage fans (i.e., fans having a plurality of stages of counter-rotating propellers).

Referring still to FIGS. 1 and 2, the exemplary aircraft 10 depicted is adapted for accomplishing a substantially vertical takeoff and/or landing, in addition to forward flight. For example, FIG. 1 depicts the aircraft 10 in a vertical takeoff mode and FIG. 2 depicts the aircraft 10 and a forward or lateral flight mode.

As will be appreciated, the exemplary aircraft 10 depicted is movable between the vertical takeoff mode and horizontal flight mode at least in part due to each wing assembly including a tilt section. For example, for the exemplary aircraft 10 depicted in FIGS. 1 and 2, the port side 30 of the forward wing assembly 26 includes a tilt section 56, the starboard side 32 of the forward wing assembly 26 includes a tilt section 58, the port side 34 of the aft wing assembly 28 includes a tilt section 60, and the starboard side 36 of the aft wing assembly 28 includes a tilt section 62. The tilt sections 56, 58, 60, 62 of the respective wing assemblies 26, 28 may be attached to respective static wing sections (not labeled) of the respective wing assemblies 26, 28 in any suitable manner. For example, the tilt sections 56, 58, 60, 62 may be attached to respective static wing sections using a swivel connection, a slip ring interface, or in any other suitable manner. Additionally, for the embodiment depicted, each of the PT fans 48, 50, 52, 54 are attached to a respective the tilt section 56, 58, 60, 62 of the respective wing assemblies 26, 28. Specifically, for the embodiment depicted, the port forward PT fan 48 is attached to the tilt section 56 of the port side 30 of the forward wing assembly 26, the starboard forward PT fan 50 is attached to the tilt section 58 of the starboard side 32 of the forward wing assembly 26, the port aft PT fan 52 is attached to the tilt section 60 of the port side 34 of the aft wing assembly 28, and the starboard aft PT fan 54 is attached to the tilt section 52 of the starboard side 36 of the aft wing assembly 28.

Figure 3:
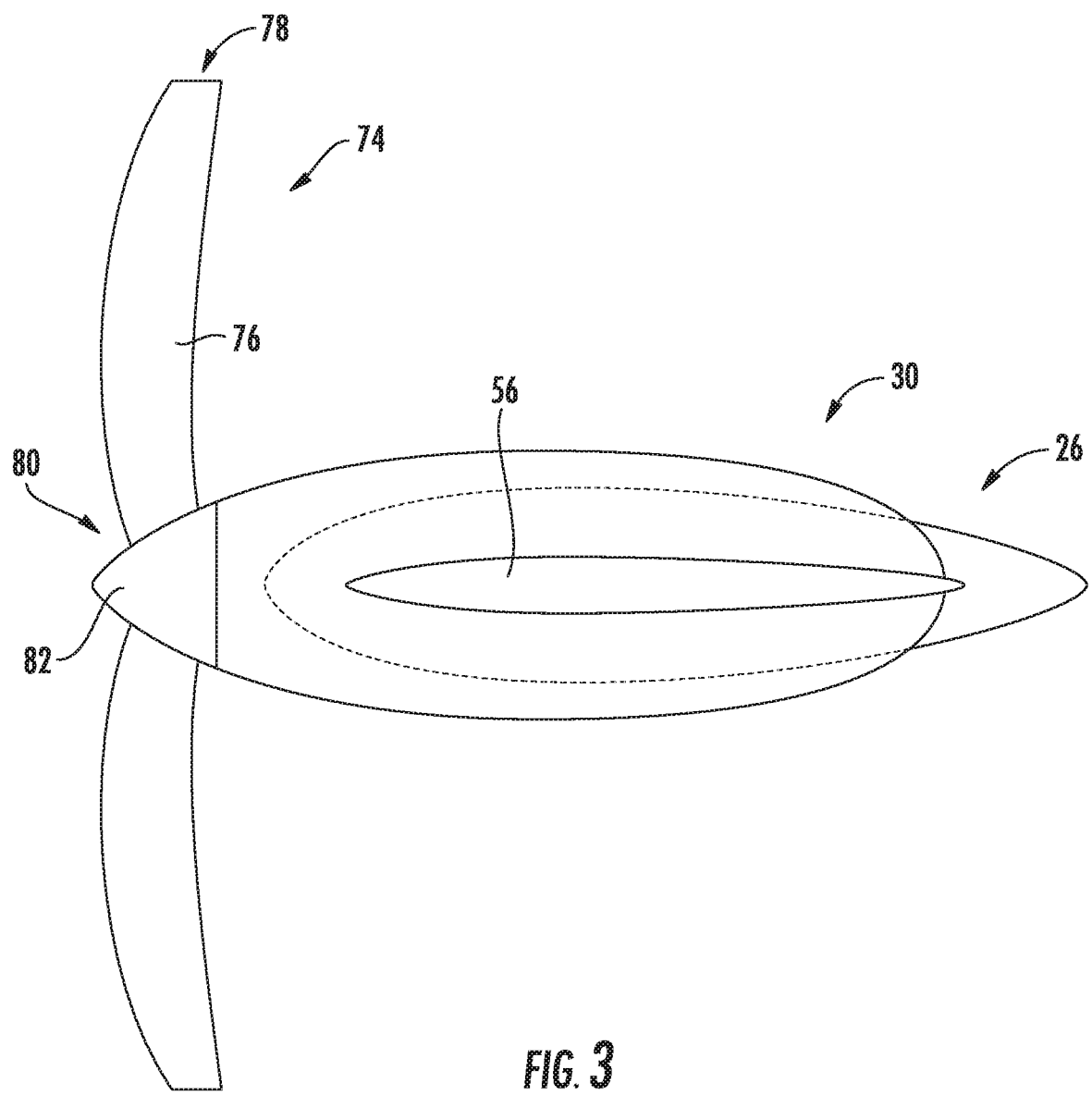
FIG. 3 is a side, schematic view of a side of a wing assembly of the exemplary aircraft of FIG. 1 in a forward thrust position.
Figure 4:
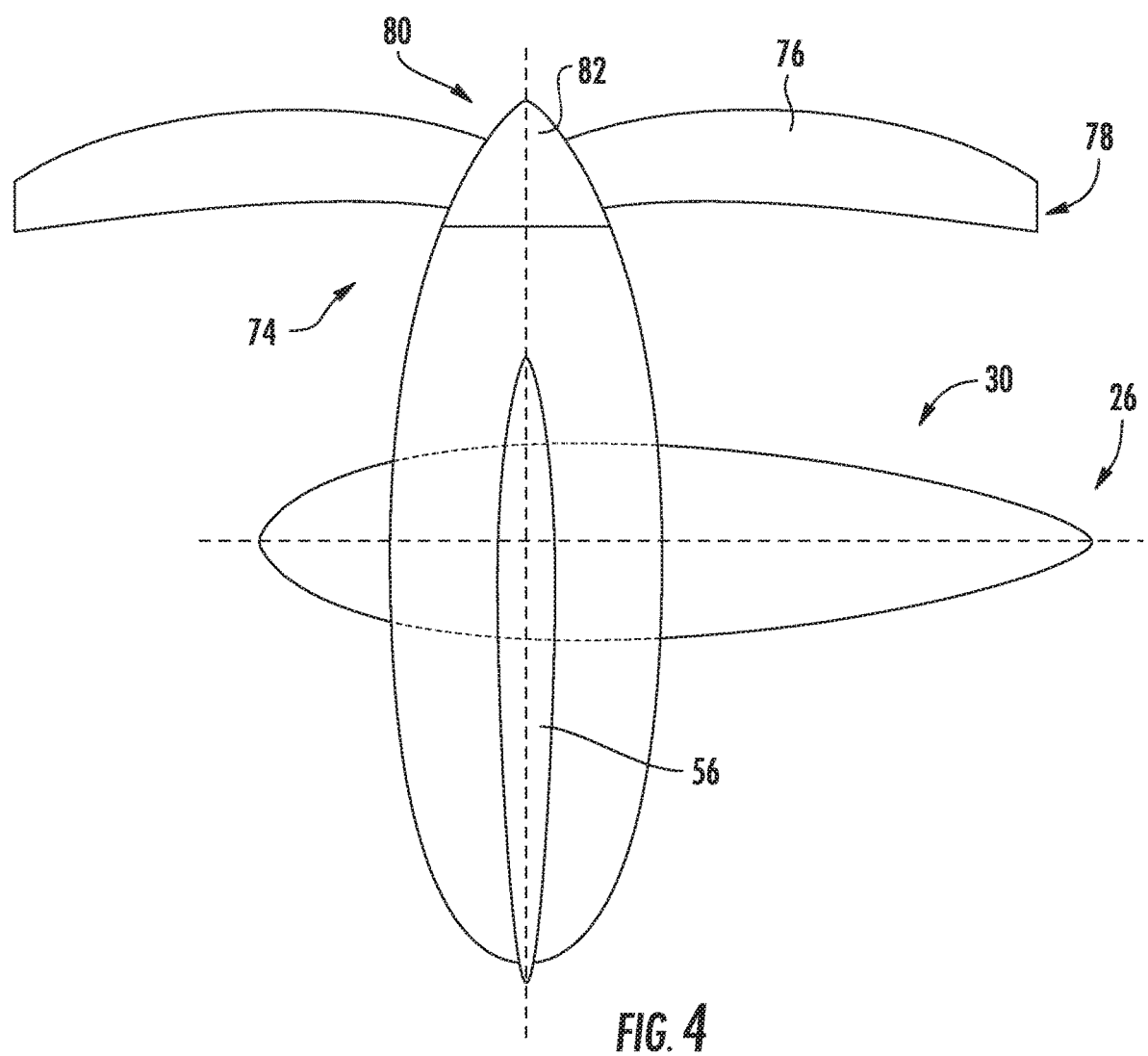
FIG. 4 is another side, schematic view of the side of the wing assembly depicted in FIG. 3 in a vertical thrust position.

Moreover, referring briefly also to FIGS. 3 and 4, side, schematic views of a side of a wing assembly of an aircraft 10 is provided in two operating modes. For example, in certain embodiments, the wing depicted may be a port side 30 of the forward wing assembly 26, described above with reference to FIGS. 1 and 2. As is depicted, each of these tilt sections 56, 58, 60, 62 is movable between a horizontal/forward flight position (FIGS. 2 and 3) and a vertical flight position (FIGS. 1 and 4). Movement of the tilt sections 56, 58, 60, 62 between the horizontal flight position and the vertical flight position additionally moves the respective PT fans 48, 50, 52, 54 between a forward thrust position and a vertical thrust position. Accordingly, each of the port and starboard forward PT fans 48, 50 and port and starboard aft PT fans 52, 54 are movable between a forward thrust position and a vertical thrust position by the respective tilt sections 56, 58, 60, 62. Specifically, each of the tilt sections 56, 58, 60, 62 rotates at least about 90° between the horizontal flight position in the vertical flight position to rotate the respective PT fans 48, 50, 52, 54 between the respective forward thrust positions and vertical thrust positions. It should be appreciated, however, that in other exemplary embodiments, the plurality of PT fans 48, 50, 52, 54 may alternatively be moveable between the forward thrust positions and the vertical thrust positions in any other suitable manner. For example, in other embodiments, one or more of the PT fans 48, 50, 52, 54 may include a hinge assembly for tilting the PT fan at least about ninety degrees between the forward thrust position and the vertical thrust position.

Referring still to FIGS. 1 and 2, the exemplary propulsion system 38 depicted further includes a plurality of relatively low diameter, secondary thrust fans ("ST fans") in addition to the plurality of PT fans 48, 50, 52, 54. For example, the exemplary propulsion system 38 depicted includes an ST fan on each wing side of each wing assembly. Specifically, the propulsion system 38 includes a port forward ST fan 64, a starboard forward ST fan 66, a port aft ST fan 68, and a starboard aft ST fan 70. For the embodiment depicted, each of the ST fans 64, 66, 68, 70 are also attached to a respective tilt section 56, 58, 60, 62 of the respective wing assemblies 26, 28. Accordingly, the port forward ST fan 64 is attached to the same tilt section 56 as the port forward PT fan 48, the starboard forward ST fan 66 is attached to the same tilt section 58 as the starboard forward PT fan 50, the port aft ST fan 68 is attached to the same tilt section 60 as port aft PT fan 52, and the starboard aft ST fan 70 is attached to the same tilt section 62 as the starboard aft PT fan 54. Accordingly, each of the ST fans 64, 66, 68, 70 are also movable between a forward thrust position and a vertical thrust position, for the embodiment depicted, by rotation of the respective tilt sections 56, 58, 60, 62 of the respective wing assemblies 26, 28. Again, however, it should be appreciated that in other exemplary embodiments one or more of the plurality of ST fans 64, 66, 68, 70 may alternatively be moveable between the forward thrust positions and the vertical thrust positions in any other suitable manner. For example, in other embodiments, one or more of the ST fans 64, 66, 68, 70 may include a hinge assembly for tilting the ST fan at least about ninety degrees between the forward thrust position and the vertical thrust position.

Moreover, for the embodiment depicted, each of the ST fans 64, 66, 68, 70 are spaced from the respective PT fans 48, 50, 52, 54 along the transverse direction T of the aircraft 10. Specifically, for the embodiment depicted, each of the ST fans 64, 66, 68, 70 are positioned farther away from the longitudinal centerline 12 of the aircraft 10 than the respective PT fans 48, 50, 52, 54. More specifically still, for the embodiment depicted, each of the ST fans 64, 66, 68, 70 are attached to an outer end of the respective wing assemblies 26, 28, along the transverse direction T.

As with the PT fans 48, 50, 52, 54, each of the plurality of ST fans 64, 66, 68, 70 are also electrically connected to the electric power source 40 via the primary electric communication bus 42 (and the secondary electric communication bus 46 for redundancy purposes). Moreover, for the embodiment depicted, each of the plurality of PT fans 48, 50, 52, 54 and each of the plurality of ST fans 64, 66, 68, 70 are configured as electric propulsors. Accordingly, each of the plurality of ST fans 64, 66, 68, 70 are electrically connected to the electric power source 40 and driven by the electric power source 40.

Figure 5:
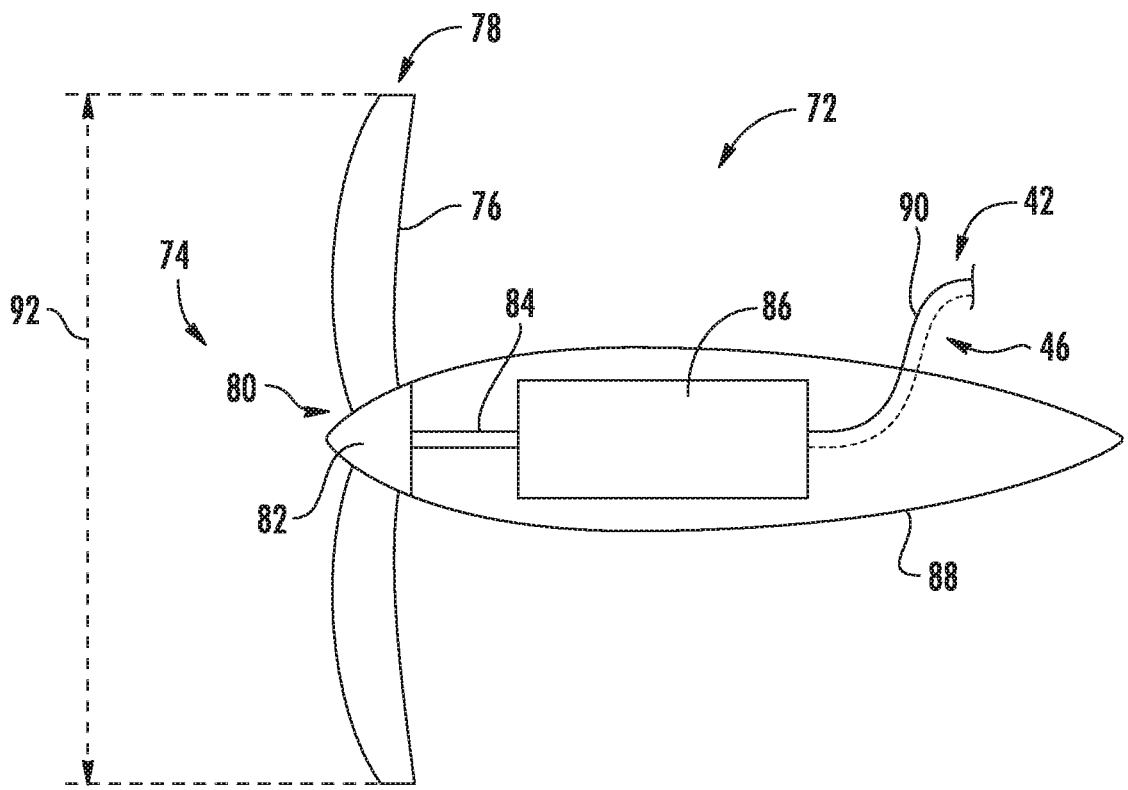
FIG. 5 is a side, schematic view of a primary thrust propulsor in accordance with an exemplary embodiment of the present disclosure.
Figure 6:
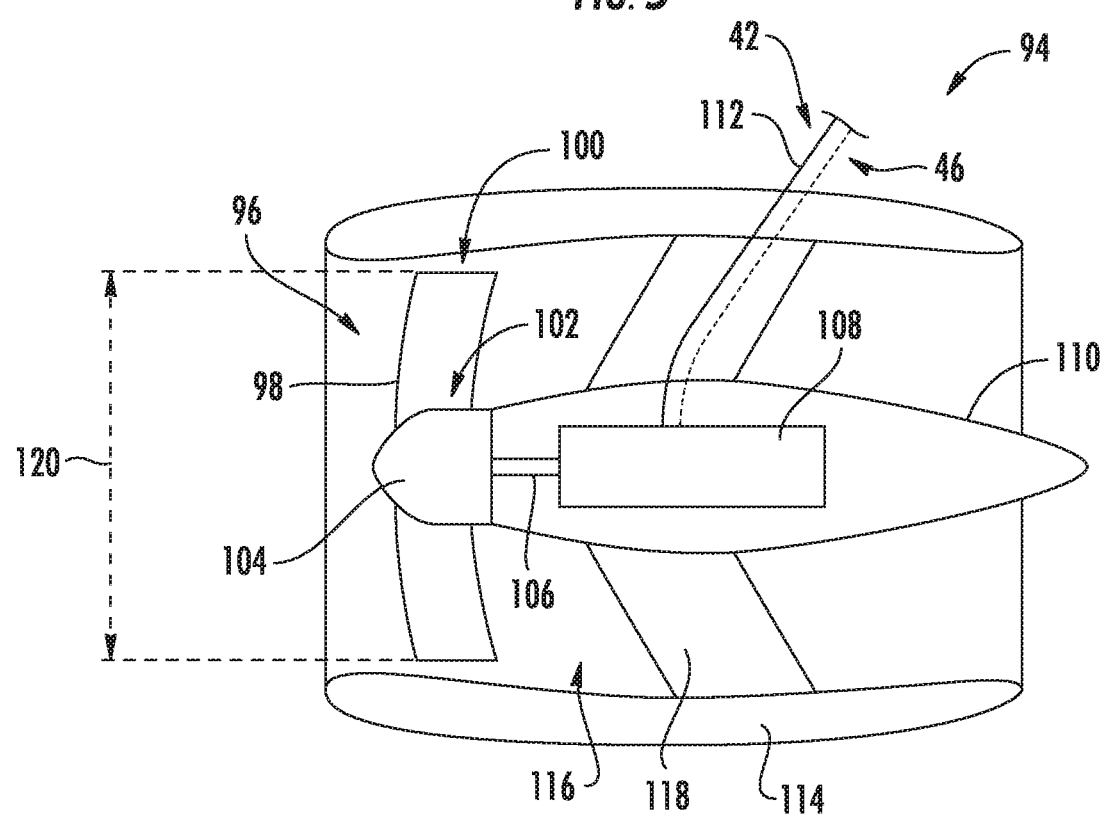
FIG. 6 is a side, schematic view of a secondary thrust propulsor in accordance with an exemplary embodiment of the present disclosure.

More specifically, referring now also to FIGS. 5 and 6, for the embodiment depicted, each of the plurality of PT fans 48, 50, 52, 54 are configured as electric fans, and each of the plurality of ST fans 64, 66, 68, 70 are also configured as electric fans. FIG. 5 provides a side, schematic view of a PT fan in accordance with an exemplary embodiment of the present disclosure, and FIG. 6 provides a side, schematic view of an ST fan in accordance with an exemplary embodiment of the present disclosure.

Referring first to FIG. 5, the exemplary PT fan is generally configured as an unducted electric fan 72. The unducted electric fan 72 generally includes a fan section 74 including a plurality of fan blades 76, with each of the plurality of fan blades 76 extending from a radially outer tip 78 to a base 80. Each of the fan blades 76 is attached to a hub 82 of the unducted electric fan 72 at the base 80. The hub 82 is attached through a fan shaft 84 to an electric motor 86 position within a cowling 88 of the unducted electric fan 72. The electric motor 86 is in electrical communication with the electric power source 40 via the primary electric communication bus 42, or more particularly, for the embodiment depicted, through an electric line 90 of the primary electric communication bus 42. Notably, the fan section 74 of the unducted electric fan 72 defines a fan diameter 92, which for the embodiment depicted refers to a diameter of a circle circumscribing the outer tips 78 of the fan blades 76 during operation of the unducted electric fan 72.

Referring now to FIG. 6, the exemplary ST fan is generally configured as a ducted electric fan 94. The ducted electric fan 94 similarly includes a fan section 96 including a plurality of fan blades 98, with each of the plurality of fan blades 98 extending from a radially outer tip 100 to a base 102. Each of the fan blades 98 is attached to a hub 104 of the ducted electric fan 94 at the base 102. The hub 104 is attached through a fan shaft 106 to an electric motor 108 positioned within a cowling 110 of the ducted electric fan 94. The electric motor 108 is in electrical communication with the electric power source 40 via the primary electric communication bus 42, or more particularly, for the embodiment depicted, through an electric line 112 of the primary electric communication bus 42. The ducted electric fan 94 further includes an outer nacelle 114 encircling the fan section 96 and the cowling 110 of the ducted electric fan 94. The cowling 110 and the outer nacelle 114 together define an airflow passage 116. A plurality of struts 118 are provided for connecting the cowling 110 to the outer nacelle 114. As with the unducted fan section 74, the ducted fan section 96 defines a fan diameter 120.

Although not depicted, one or both of the unducted electric fan 72 or ducted electric fan 94 may additionally include a gearbox between a respective electric motor 86, 108 and fan section 74, 96 for increasing or decreasing a rotational speed of the respective fan relative section to the respective electric motor 86, 108. Moreover, in certain embodiments, one or both of the unducted electric fan 72 or ducted electric fan 94 may include one or more mechanisms for varying a pitch of each of the plurality of fan blades 76, 98 during operation.

In certain embodiments, the unducted fan 72 may define the relatively high fan diameter 92 as compared to the ducted fan 94. Additionally, the unducted fan 72 may be configured to generate a relatively high amounts of thrust as compared to the ducted fan 94. Accordingly, the unducted fan 72 may be utilized as a primary source of thrust during takeoff operating conditions or other vertical flight operations. By contrast, the ducted fans 94 may have a relatively low fan diameter 120 and may generate a relatively low amount of thrust. However, the ducted fans 94 may operate more efficiently than the unducted fans 72 during certain flight operations. Accordingly, the ducted fans 94 may be utilize as a primary source of thrust during, e.g., forward flight operations, such as during cruise operations.

However, as will be appreciated, in other embodiments, one or more of the plurality of ST fans 64, 66, 68, 70 may be used in addition to the plurality of PT fans 48, 50, 52, 54 during vertical lift/flight conditions, and additionally or alternatively, one or more of the plurality of PT fans 48, 50, 52, 54 may be used in addition to the plurality of ST fans 64, 66, 68, 70 during horizontal/forward flight conditions. Additionally, as will be discussed with reference to one or more of the figures below, in certain embodiments, the propulsion system 38 may not include each of the plurality of ST fans 64, 66, 68, 70, may not include each of the plurality of PT fans 48, 50, 52, 54, or may include any other suitable number/form of electric propulsion devices.

Referring still to FIGS. 1 and 2, for the embodiment depicted, the electric power source 40 is located remotely from the electric propulsors, within the fuselage 18 of the aircraft 10 proximate the aft end 22 of the fuselage 18. Notably, however, in other embodiments the electric power source 40 may instead be located at any other suitable location within the fuselage 18 of the aircraft 10, or elsewhere. Additionally, the electric power source 40 generally includes a combustion engine and an electric generator 122 driven by the combustion engine for generating electrical power. The combustion engine and electric generator are mounted, for the embodiment depicted, within the fuselage 18 of the aircraft 10, proximate the aft end 22 of the fuselage 18. During operation, the primary electric communication bus 42 connects the electric generator 122 to each of the above described electric propulsors.

Figure 7:
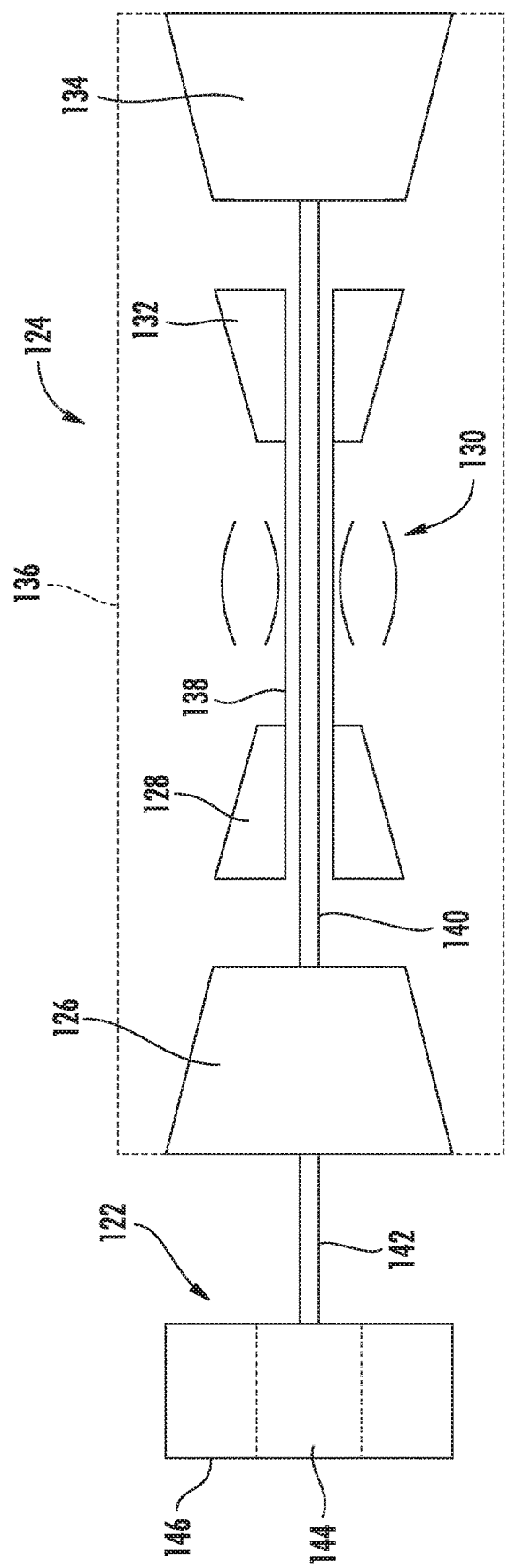
FIG. 7 is a schematic view of an electric power source in accordance with an exemplary embodiment of the present disclosure.

Referring now also to FIG. 7, a schematic view of the exemplary combustion engine and the electric generator 122 is provided. For the embodiment depicted, the combustion engine is configured as a turboshaft engine 124. The turboshaft engine 124 includes in serial flow order, a compressor section including a low pressure compressor 126 and a high pressure compressor 128, a combustion section 130, and a turbine section including a high pressure turbine 132 and a low pressure turbine 134. During operation, a flow of air is received within the compressor section and is progressively compressed as it flows therethrough, i.e., as it flows from the low pressure compressor 126 to the high pressure compressor 128. The compressed air is then provided to the combustion section 130 where it is mixed with fuel and burned to generate hot combustion gas. The hot combustion gas is expanded through the turbine section where rotational energy is extracted therefrom. Specifically, the hot combustion gas rotates the high pressure turbine 132 and the low pressure turbine 134 as the gas flows therethrough and is expanded. As is depicted in phantom, these components may be enclosed within a casing 136 within, e.g., the fuselage 18 of the aircraft 10. Although not depicted, the hot combustion gas may be exhausted, e.g., to atmosphere, from the low pressure turbine 134.

As is also depicted, for the embodiment depicted, the high pressure turbine 132 is connected to the high pressure compressor 128 through a high pressure shaft or spool 138, such that a rotation of the high pressure turbine 132 additionally rotates the high pressure compressor 128. Similarly, the low pressure turbine 134 is connected to the low pressure compressor 126 through a low pressure shaft or spool 140, such that rotation of the low pressure turbine 134 additionally rotates the low pressure compressor 126. Moreover, for the embodiment depicted, the low pressure shaft 140 additionally drives an output shaft 142 extending to the electric generator 122. Accordingly, a rotation of the turboshaft engine 124 provides rotational energy to the electric generator 122, the electric generator 122 configured to convert the rotational energy to generate electrical power. As will be appreciated, in certain embodiments, the electric generator 122 may generally include a rotor 144 and a stator 146. The rotational energy of the turboshaft engine 124 is provided via the output shaft 142 and configured to rotate the rotor 144 of the electric generator 122 relative to the stator 146. Such relative movement may generate electrical power.

Inclusion of a turboshaft engine 124 and electric generator 122 in accordance with such an exemplary embodiment may allow for the electric power source 40 to generate a relatively high amount of electric power and to provide such electric power to the plurality of electric propulsors of the propulsion system 38. For example, in at least certain exemplary embodiments, the turboshaft engine 124 may be a relatively large turboshaft engine 124 configured to generate at least about 1000 horsepower ("hp"), such that the electric generator 122 generates at least about 0.75 megawatt ("MW"). Specifically, in certain embodiments the turboshaft engine 124 may be configured to generate at least about 1320 hp, such that the electric generator 122 generates at least about 9.69 MW, such as at least about 1500 hp, such that the electric generator 122 generates at least about 1.12 MW, such as at least about 1660 hp, such that the electric generator 122 generates at least about 1.4 MW. It should be appreciated, that as used herein, terms of approximation, such as a "about" or "approximately," refers to being within 10% margin of error.

In at least certain embodiments, the propulsion system 38 may be configured such that the turboshaft engine 124 and electric generator 122 are capable of generating a sufficient amount of electrical power to drive each of the electric propulsors of the propulsion system 38 simultaneously. By way of example only, for the embodiment where the turboshaft engine 124 generates about 1660 hp, and the generator generates about 1.4 MW, each of the four PT fans 48, 50, 52, 54 may include 175 kW electric motors and similarly, each of the ST fans 64, 66, 68, 70 may include 175 kW electric motors. Accordingly, with such an embodiment, the electric propulsion system 38 may be configured to substantially fully power each of the electric propulsors during certain operations, such as during takeoff or other vertical thrust operations.

By contrast, in other embodiments, the propulsion system 38 may be configured such that the turboshaft engine 124 and electric generator 122 is not capable of simultaneously fully powering each of the electric propulsors included. By way of example only, for the embodiment where the turboshaft engine 124 generates about 1660 hp, and the generator generates about 1.4 MW, each of the four PT fans 48, 50, 52, 54 may include 350 kW electric motors and similarly each of the ST fans 64, 66, 68, 70 may include 350 kW electric motors. Accordingly, with such an embodiment, the plurality of PT fans 48, 50, 52, 54 may be configured to operate during a takeoff or other vertical thrust operation, while the plurality of ST fans 64, 66, 68, 70 may be configured to operate during forward thrust operations. Additionally, or alternatively, a supplemental power source may be used to drive certain of the propulsors during these "peak" operations. For example, in certain embodiments, the turboshaft engine 124 and electric generator 122, in combination with the one or more energy storage devices 44 of the propulsion system 38, may be used to drive the four PT fans 48, 50, 52, 54, in addition to one or more of the ST fans 64, 66, 68, 70.

It should be appreciated, however, that the exemplary turboshaft engine 124 depicted is provided by way of example only, and that in other exemplary embodiments, the turboshaft engine 124 may have any other suitable configuration. For example, in other embodiments, the turboshaft engine 124 may include any other suitable number of compressors or turbines, as well as any other suitable number or configuration of shafts or spools.

Figure 8:
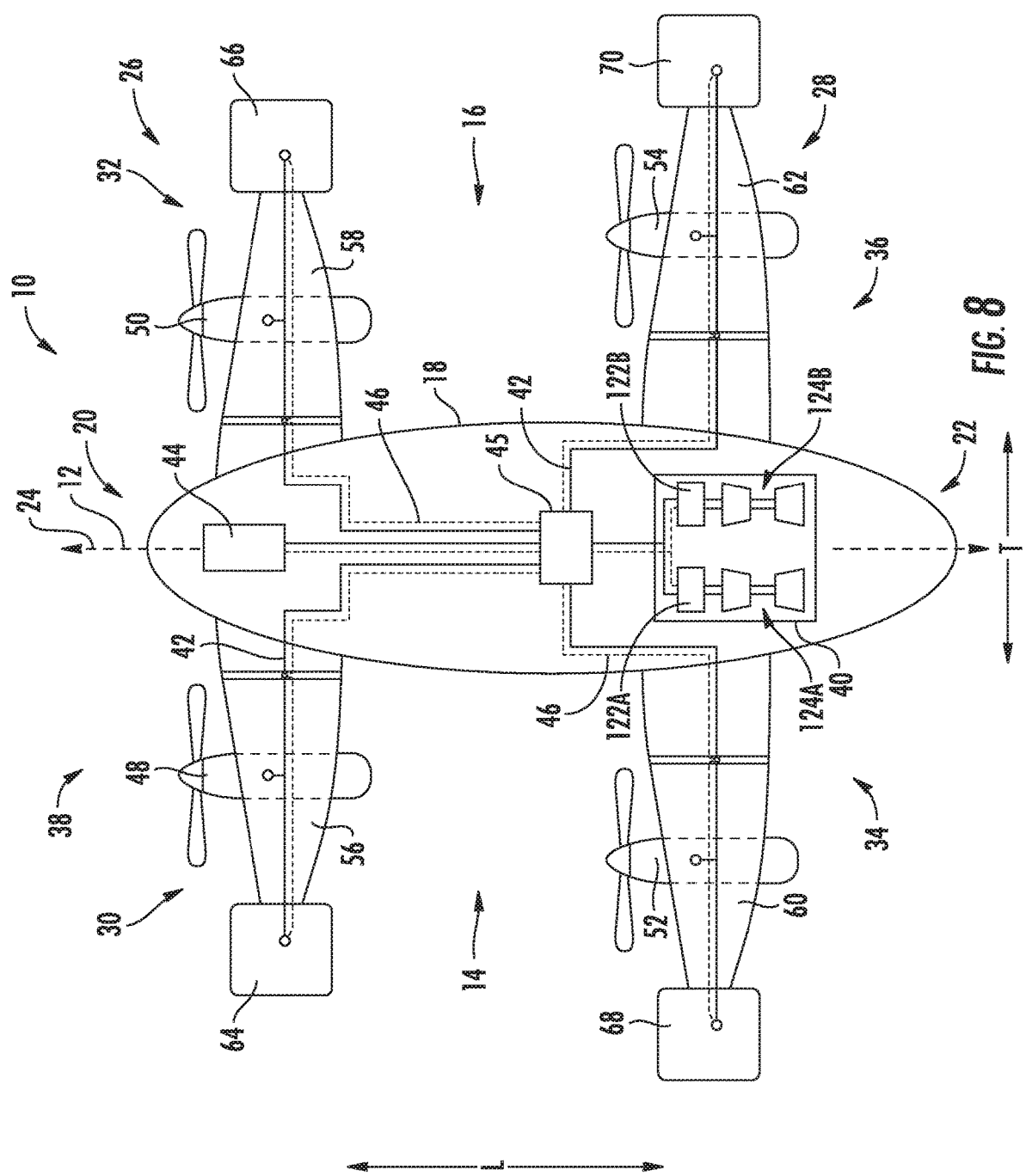
FIG. 8 is a top, schematic view of an aircraft in accordance with another exemplary embodiment of the present disclosure.

Moreover, it should be appreciated, that in still other embodiments, the electric power source 40 may also have any other suitable configuration. For example, referring now to FIG. 8, an aircraft 10 and propulsion system 38 in accordance with another exemplary embodiment of the present disclosure is provided. The exemplary propulsion system 38 depicted in FIG. 8 may be configured in substantially the same manner as exemplary propulsion system 38 depicted in FIGS. 1 and 2 described above. Accordingly, the same numbers may refer to the same or similar part.

For example, as is depicted, the aircraft 10 generally includes a fuselage 18, with a forward wing assembly 26 attached to the fuselage 18 proximate a forward end 20 of the fuselage 18 and an aft wing assembly 28 attached to the fuselage 18 proximate an aft end 22 of the fuselage 18. The forward wing assembly 26 includes a port section with a port forward PT fan 48 and a port forward ST fan 64 attached thereto, and a starboard section with a starboard forward PT fan 50 and a starboard forward ST fan 66 attached thereto. The aft wing assembly 28 similarly includes a port section with a port aft PT fan 52 and a port aft ST fan 68 attached thereto, and a starboard section with a starboard aft PT fan 54 and a starboard aft of the fan attached thereto.

Additionally, the propulsion system 38 includes an electric power source 40. The electric power source 40 generally includes a combustion engine and a generator 122. However, for the embodiment depicted, the electric power source 40 further includes a plurality of combustion engines and a respective plurality of generators 122. Specifically, for the embodiment depicted, the electric power source 40 includes a first turboshaft engine 124A and a second turboshaft engine 124B. The first turboshaft engine 124A drives a first electric generator 122A and the second turboshaft engine 124B drives a second electric generator 122B. The first and second turboshaft engines 124A, 124B and first and second electric generators 122A, 122B may be configured in substantially the same manner as exemplary turboshaft engine 124 and electric generator 122 described above with reference to FIG. 7. Such a configuration may allow the electric power source 40 to provide the propulsion system 38 with a necessary amount of electric power, and may also provide for a redundancy in the propulsion system 38.

Referring again to FIGS. 1 and 2, for the embodiment depicted, the propulsion system 38 of the exemplary aircraft 10 depicted is configured as a substantially balanced propulsion system 38. For example, the propulsion system 38 includes two forward PT fans (i.e., the port and starboard forward PT fans 48, 50) and two forward ST fans (i.e., the port and starboard forward ST fans 64, 66), as well as two aft PT fans (i.e., the port and starboard aft PT fans, 52, 54) and two aft ST fans (i.e., the port and starboard aft ST fans 68, 70). The port and starboard forward PT fans 48, 50 each define a forward PT fan diameter 148 and the port and starboard forward ST fans 64, 66 each define a forward ST fan diameter 150. Similarly, the port and starboard aft PT fans 52, 54 each define an aft PT fan diameter 154 and the port and starboard aft ST fans 68, 70 each define an aft ST fan diameter 156. For the embodiment depicted, the forward PT fan diameter 148 is substantially the same as the aft PT fan diameter 154, and the forward ST fan diameter 150 is substantially the same as the aft ST fan diameter 156.

Moreover, for the embodiment depicted, the forward PT fans 48, 50 together define a maximum forward PT thrust capability and the aft PT fans 52, 54 also define a maximum aft PT thrust capability. Similarly for the embodiment depicted, the forward ST fans 64, 66 together define a maximum forward ST thrust capability and the aft ST fans 68, 70 also define a maximum aft ST thrust capability. For the embodiment depicted, the maximum forward PT thrust capability is substantially the same as the maximum aft PT thrust capability, and the maximum forward ST thrust capability is also substantially the same as the maximum aft ST thrust capability.

Additionally, it will be appreciated that the exemplary aircraft 10 depicted defines a minimum necessary takeoff thrust. The minimum necessary takeoff thrust refers to a minimum amount of vertical thrust required for the aircraft 10 to perform a vertical takeoff when carrying a maximum rated weight of cargo. In certain embodiments, the maximum forward PT thrust capability and the maximum aft PT thrust capability together may be greater than or equal to the minimum necessary takeoff thrust of the aircraft 10. However, in other embodiments, the maximum forward PT thrust capability and the maximum aft PT thrust capability together may not be greater than or equal to the minimum necessary takeoff thrust of the aircraft 10. For such exemplary embodiments, however, the maximum forward PT thrust capability and the maximum aft PT thrust capability, together with the maximum forward ST thrust capability and the maximum aft ST thrust capability, is greater than or equal to the minimum necessary takeoff thrust of the aircraft 10.

It should be appreciated, however, that in other embodiments, the aircraft 10 and propulsion system 38 may instead have any other suitable configuration. For example, referring now to FIG. 9, an aircraft 10 and propulsion system 38 in accordance with another exemplary embodiment of the present disclosure is provided. The exemplary propulsion system 38 depicted in FIG. 9 may be configured in substantially the same manner as exemplary propulsion system 38 depicted in FIGS. 1 and 2 described above. Accordingly, the same numbers may refer to the same or similar part.

For example, as is depicted, the aircraft 10 generally includes a fuselage 18, with a forward wing assembly 26 attached to the fuselage 18 proximate a forward end 20 of the fuselage 18 and an aft wing assembly 28 attached to the fuselage 18 proximate an aft end 22 of the fuselage 18. The forward wing assembly 26 includes a port section with a port forward PT fan 48 and a port forward ST fan 64 attached thereto, and a starboard section with a starboard forward PT fan 50 and a starboard forward ST fan 66 attached thereto. The aft wing assembly 28 similarly includes a port section with a port aft PT fan 52 and a port aft ST fan 68 attached thereto, and a starboard section with a starboard aft PT fan 54 and a starboard aft of the fan attached thereto.

The port and starboard forward PT fans 48, 50 each define a forward PT fan diameter 148. Similarly, the port and starboard aft PT fans 52, 54 each define an aft PT fan diameter 154. Additionally, the forward PT fans 48, 50 together define a maximum forward PT thrust capability and the aft PT fans 52, 54 also define a maximum aft PT thrust capability. However, for the embodiment depicted, the forward PT fan diameter 148 is different than the aft PT fan diameter 154. Specifically, for the embodiment depicted, the aft PT fan diameter 154 is greater than the forward PT fan diameter 148. Moreover, for the embodiment depicted, the maximum forward PT thrust capability is different than the maximum aft PT thrust capability. More specifically, for the embodiment depicted, the maximum aft PT thrust capability is greater than the maximum forward PT thrust capability.

Notably, the forward ST fans 64, 66 together define a maximum forward ST thrust capability and the aft ST fans 68, 70 also define a maximum aft ST thrust capability. For the embodiment depicted, the forward ST thrust capability is substantially the same as the aft ST thrust capability.

It should be appreciated, however, that despite the differences in maximum thrust capabilities, in at least certain embodiments, the maximum forward PT thrust capability of the forward PT fans 48, 50 and maximum aft PT thrust capability of the aft PT fans 52, 54 may still be greater than or equal to a minimum necessary takeoff thrust for the aircraft 10. The imbalance of the maximum thrust capabilities between the forward PT fans 48, 50 and aft PT fans 52, 54 may be due at least in part to a weight distribution of the aircraft 10 or a relative positioning of the forward wing assembly 26 and aft wing assembly 28. Additionally, or alternatively, the aft PT fans 52, 54 may simply be larger or more powerful to provide for a greater maximum speed of the aircraft 10.

Figure 10:
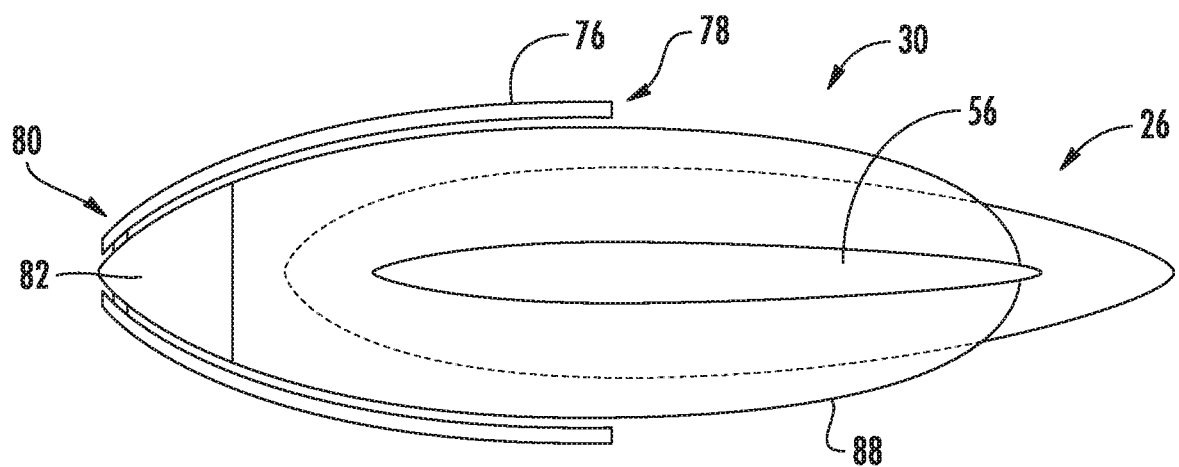
FIG. 10 is a side, schematic view of a side of a wing assembly of an aircraft in accordance with an exemplary embodiment of the present disclosure.

Referring briefly now also to FIG. 10, providing a schematic view of a wing section of a wing assembly of an aircraft 10, it should be appreciated that in certain embodiments, one or both of the forward PT fans 48, 50 or aft PT fans 52, 54 are not be required to operate during certain flight conditions. For example, during, e.g., cruise operations, the aircraft 10 may receive a desired amount of forward thrust from one or both of the forward ST fans 64, 66 or aft ST fans 68, 70. With such an embodiment, at least certain of the PT fans 48, 50, 52, 54 may include a plurality of fan blades 76 that are movable from an extended position to a stowed position in order to reduce an amount of drag on the aircraft 10 from such fan blades 76 when the respective fan is not in use. For example, as is depicted in FIG. 10, the one or more fan blades 76 may fold back adjacent to a core cowling 88 of the fan, such that the fan blades 76 create less drag on the aircraft 10. It should be appreciated, however, that in other embodiments, the fan blades 76 may not fold back when moved from the extended position to the stowed position, and instead may be configured to at least partially retract, or may be configured to be feathered (i.e., rotated such that a pitch angle of the blades 76 is parallel to an airflow direction).

Notably, in other embodiments the present disclosure, the propulsion system 38 may not include all of the propulsors described above. For example, referring now to FIG. 11, providing a schematic view of a propulsion system 38 in accordance with another exemplary embodiment of the present disclosure, the propulsion system 38 does not include aft ST fans 68, 70. In other respects, however, the propulsion system 38 of FIG. 11 may be configured in substantially the same manner as the propulsion system 38 described above with reference to FIG. 9. The exemplary aircraft 10 and propulsion system 38 depicted in FIG. 11 may be designed with propulsors capable of taking off, while also being designed for efficient cruising operations. For example, a maximum aft PT thrust capability of the aft PT fans 52, 54 may be greater than a maximum forward PT thrust capability of the forward PT fans 48, 50. Moreover, for at least certain exemplary embodiments, a combination of the maximum thrust capabilities of the forward PT fans 48, 50 and the aft PT fans 52, 54 may be less than a minimum necessary takeoff thrust for the aircraft 10. However, for such an exemplary embodiment, the forward ST fans 64, 66 may be configured to assist with takeoff operations. Accordingly, with such an embodiment, a maximum thrust capability of the forward ST fans 64, 66, the forward PT fans 48, 50, and aft PT fans 52, 54 may be together be greater than or equal to a minimum necessary takeoff thrust for the aircraft 10.

Figure 9:
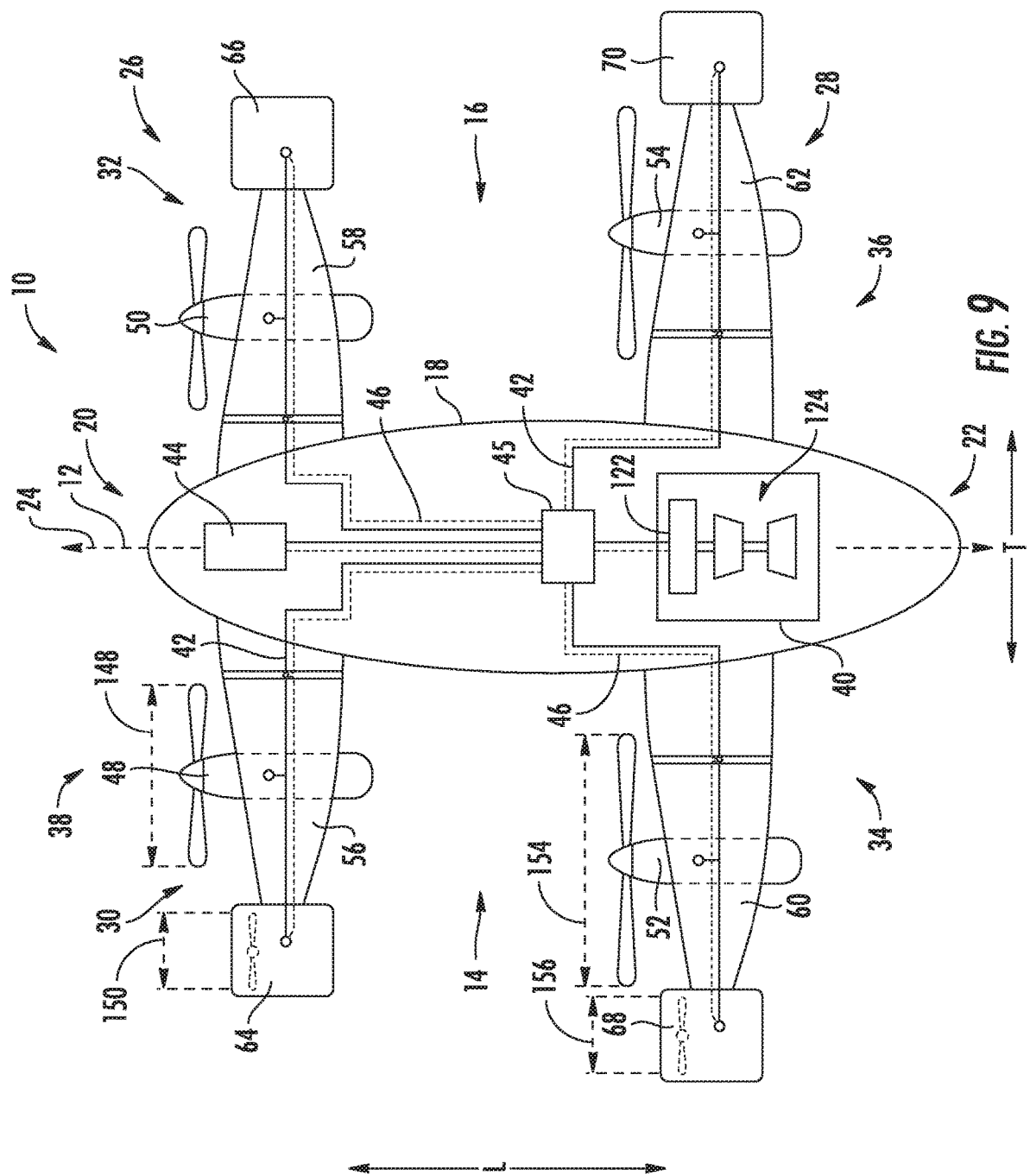
FIG. 9 is a top, schematic view of an aircraft in accordance with yet another exemplary embodiment of the present disclosure.
Figure 11:
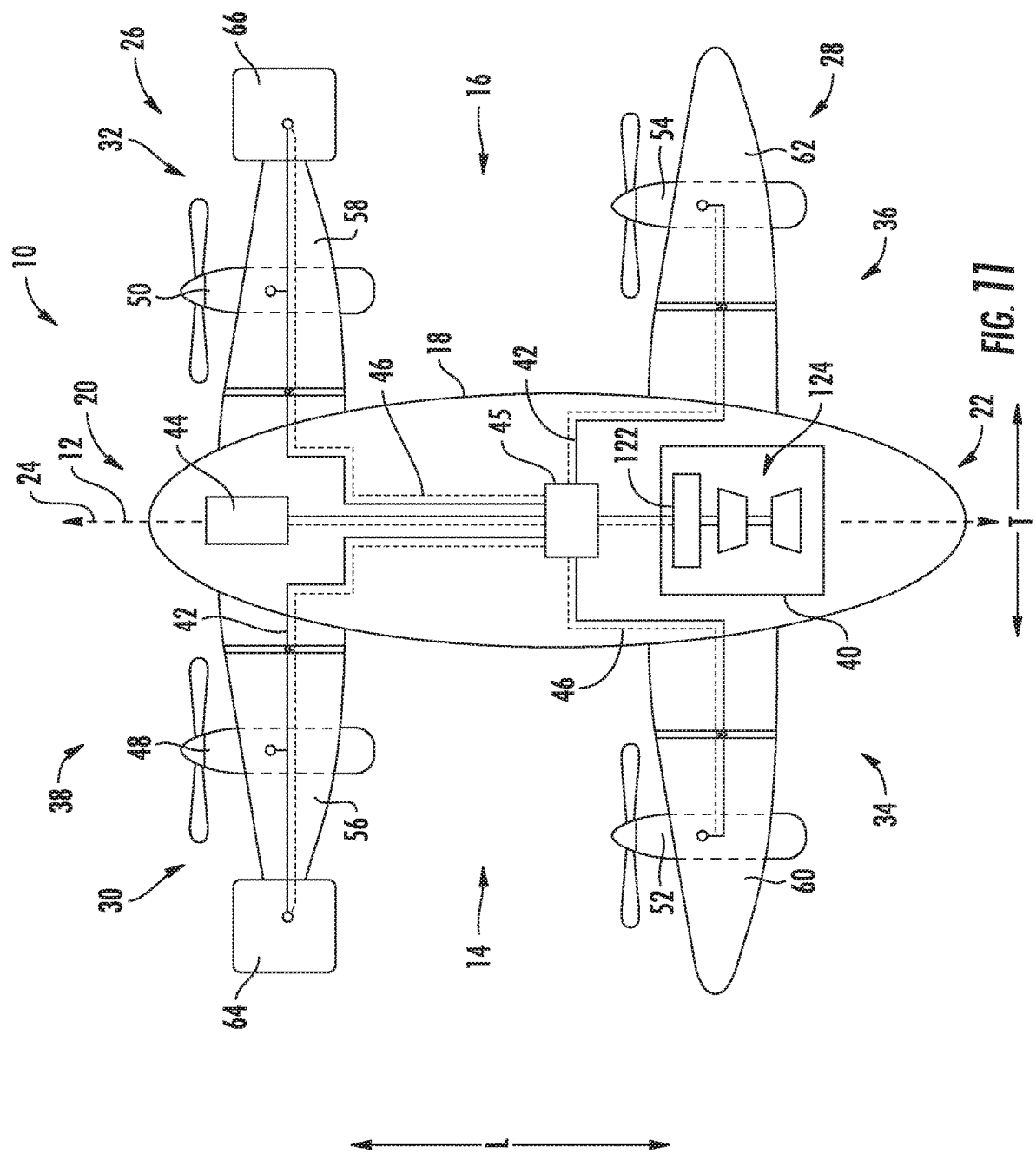
FIG. 11 is a top, schematic view of an aircraft in accordance with still another exemplary embodiment of the present disclosure.

It should further be appreciated, that the embodiments depicted in FIGS. 9 and 11 are also by way of example only. For example, in other embodiments the forward PT fans 48, 50 may instead define a greater maximum thrust capability and a greater fan diameter than the maximum thrust capability and fan diameter of the aft PT fans 52, 54. Further, in such an embodiment, the aircraft 10 may or may not include the forward ST fans 64, 66, and instead may include aft ST fans 68, 70.

Moreover, it should be appreciated, that in still other embodiments, the propulsion system 38 may not include any ST fans mounted to the forward wing assembly 26 and/or aft wing assembly 28. Additionally, or alternatively, the propulsion system 38 may not include any PT fans mounted to the forward wing assembly 26 and/or the aft wing assembly 28. For example, in certain embodiments, the propulsion system 38 may include PT fans attached to one of the forward wing assembly 26 or aft wing assembly 28, and ST fans attached to the other of the forward wing assembly 26 or the aft wing assembly 28. Additionally, or alternatively still, the propulsion system 38 may include a greater number of PT fans or ST fans on one or both of the forward wing assembly 26 and/or aft wing assembly 28.

Figure 12:
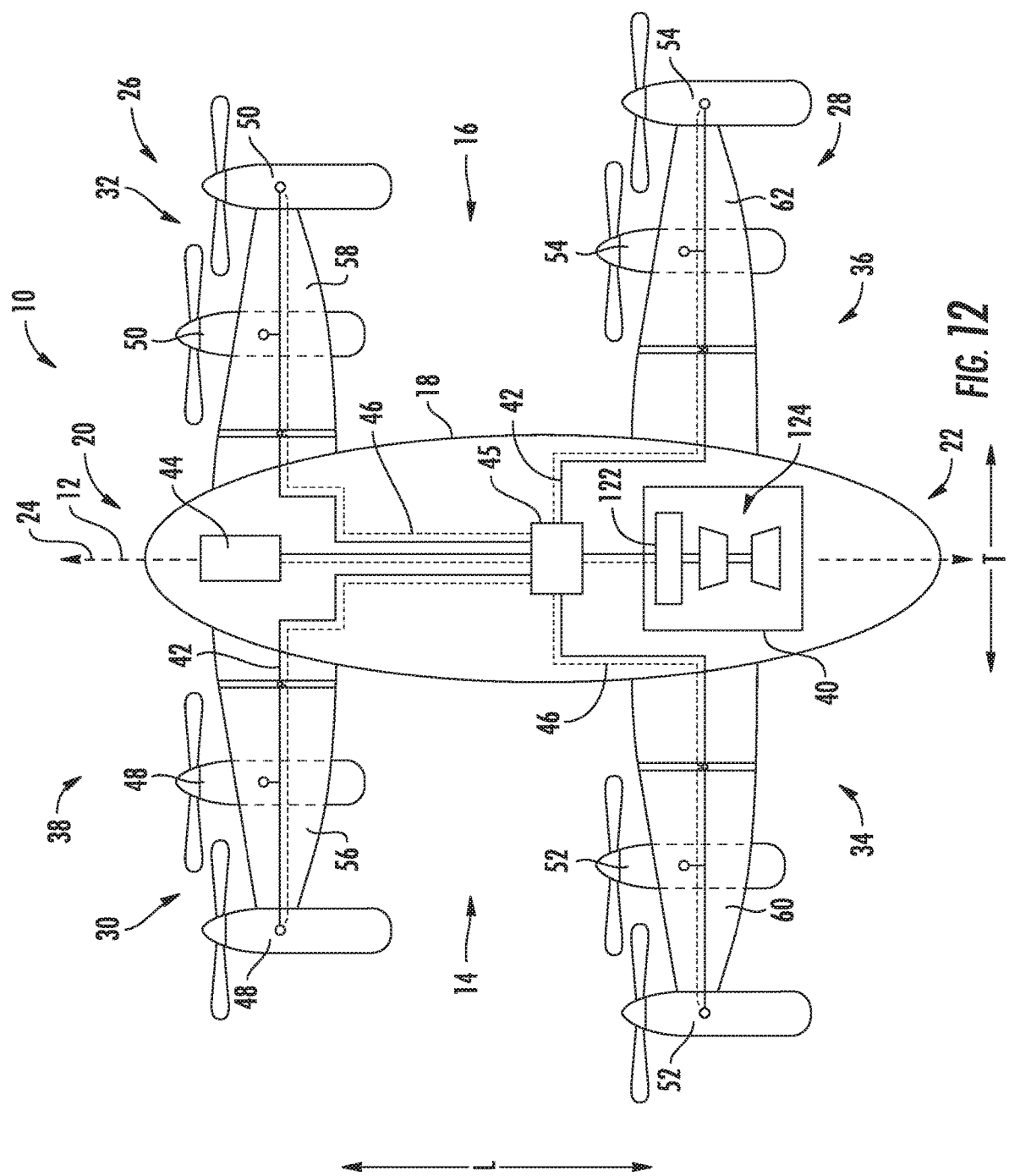
FIG. 12 is a top, schematic view of an aircraft in accordance with yet another exemplary embodiment of the present disclosure.

For example, referring now to FIG. 12, a propulsion system 38 of an aircraft 10 in accordance with another exemplary embodiment of the present disclosure is depicted. The exemplary propulsion system 38 depicted in FIG. 12 may be configured in substantially the same manner as exemplary propulsion system 38 described above with reference to FIGS. 1 and 2. Accordingly, the same numbers may refer to the same or similar parts.

As is depicted, the aircraft 10 generally includes a fuselage 18 extending between a forward end 20 and aft end 22, with a forward wing assembly 26 attached to the fuselage 18 proximate the forward end 20 and an aft wing assembly 28 attached the fuselage 18 proximate the aft end 22. The propulsion system 38 additionally includes a port forward PT fan 48, a starboard forward PT fan 50, a port aft PT fan 52, and a starboard aft PT fan 54. However, for the embodiment depicted, each of the PT fans are instead configured as a plurality of PT fans. More specifically, for the embodiment depicted, the port forward PT fan 48 includes a plurality of PT fans, the starboard forward PT fan 50 includes a plurality of PT fans, the port aft PT fan 52 includes a plurality of PT fans, and the starboard aft PT fan 54 includes a plurality of PT fans. More specifically, still, for the embodiment of FIG. 12, the port forward PT fan 48 includes a pair of PT fans, the starboard forward PT fan 50 includes a pair of PT fans, the port aft PT fan 52 includes a pair of PT fans, and the starboard aft PT fan 54 includes a pair of PT fans.

Although the propulsion system 38 of FIG. 12 includes two fans mounted to each of the port and starboard sides of the forward and aft wing assemblies 26, 28, in other embodiments, the propulsion system 38 may instead include any other suitable number of fans mounted to the wing assemblies. For example, in certain embodiments, the propulsion system 38 may include a plurality of PT fans and/or ST fans mounted to each of the port and starboard sides 30, 32, 34, 36 of one of the forward wing assembly 26 or aft wing assembly 28, and a different number of PT fans and/or ST fans mounted to the port and starboard sides 30, 32, 34, 36 of the other of the forward wing assembly 26 or aft wing assembly 28.

Further still, in other embodiments, the propulsion system 38 may have any other suitable type of propulsors. For example, referring now to FIG. 13, a propulsion system 38 for an aircraft 10 in accordance with yet another exemplary embodiment of the present disclosure is depicted. The exemplary propulsion system 38 and aircraft 10 of FIG. 13 may be configured in substantially the same manner as exemplary propulsion system 38 described above with reference to FIGS. 1 and 2. Accordingly, the same numbers may refer to the same or similar part.

For example, the aircraft 10 generally includes a fuselage 18 extending between a forward end 20 and an aft end 22 generally along a longitudinal centerline 12. A forward wing assembly 26 is attached to the fuselage 18 proximate the forward end 20 of the fuselage 18 and an aft wing assembly 28 is attached to the fuselage 18 proximate the aft end 22 of the fuselage 18. The exemplary propulsion system 38 includes a plurality of propulsors attached to one or both of the forward wing assembly 26 and the aft wing assembly 28. More particularly, for the embodiment depicted, the propulsion system 38 includes a plurality of port side propulsors (e.g., a port forward PT fan 48, a port aft PT fan 52, a port forward ST fan 64, and a port aft ST fan 68) and a plurality of starboard side propulsors (e.g., a starboard forward PT fan 50, a starboard aft PT fan 54, a starboard forward ST fan 66, and a starboard aft ST fan 70). Each of these propulsors is in electrical communication with a remotely positioned electric power source 40 via a primary electric communication bus 42 and a secondary electric communication bus 46.

Moreover, for the embodiment depicted, the exemplary propulsion system 38 further includes a supplemental propulsor mounted to the fuselage 18 of the aircraft 10. For the embodiment depicted, the supplemental propulsor is configured as an aft fan 158, and more particularly, a ducted aft fan attached to the fuselage 18 at the aft end 22 of the fuselage 18. However, by contrast with the other propulsors of the propulsion system 38, the aft fan 158 is mechanically coupled to the combustion engine (i.e., the turboshaft engine 124) via a supplemental fan shaft 160. As is depicted in phantom, the propulsion system 38 may include a gearbox 162 through which the aft fan 158 is mechanically coupled to the turboshaft engine 124. The gearbox 162 may be a reduction gearbox for reducing rotational speed of the aft fan 158 relative to the turboshaft engine 124, or alternatively, the gearbox 162 may increase a rotational speed of the aft fan 158 relative to the turboshaft engine 124. As is also depicted in phantom, the propulsion system 38 may additionally include a coupling unit 164, such that the aft fan 158 is selectively mechanically coupled to the turboshaft engine 124 through the coupling unit 164. The coupling unit 164 may include, e.g., a clutch or other similar coupling means. Moreover, in certain embodiments, the propulsion system 38 may additionally include one or more gears, such offset gears, linkages, etc. (not shown) for mechanically coupling the aft fan 158 to the turboshaft engine 124 via the aft fan 158 shaft 160.

Figure 13:
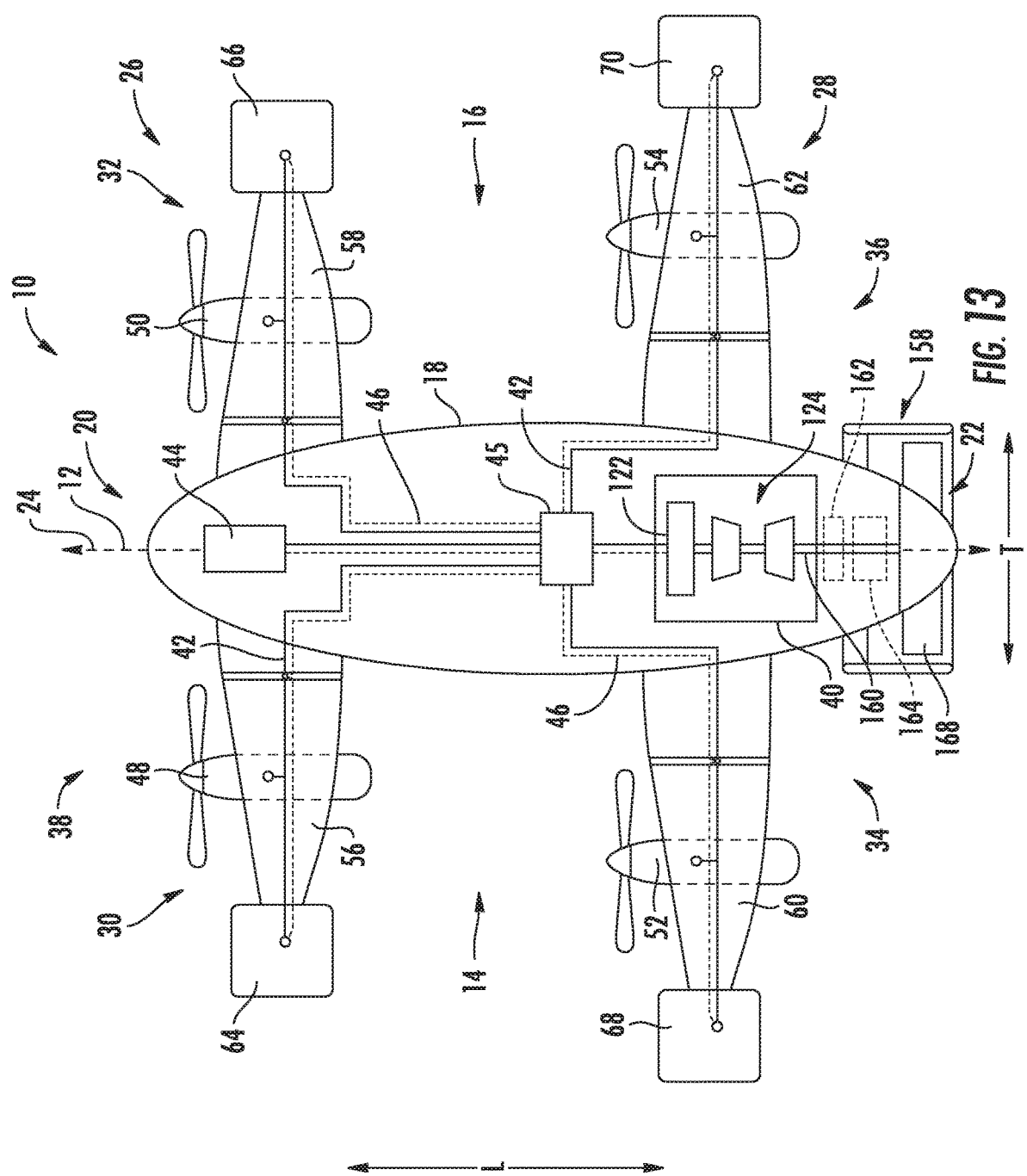
FIG. 13 is a top, schematic view of an aircraft in accordance with still another exemplary embodiment of the present disclosure.
Figure 14:
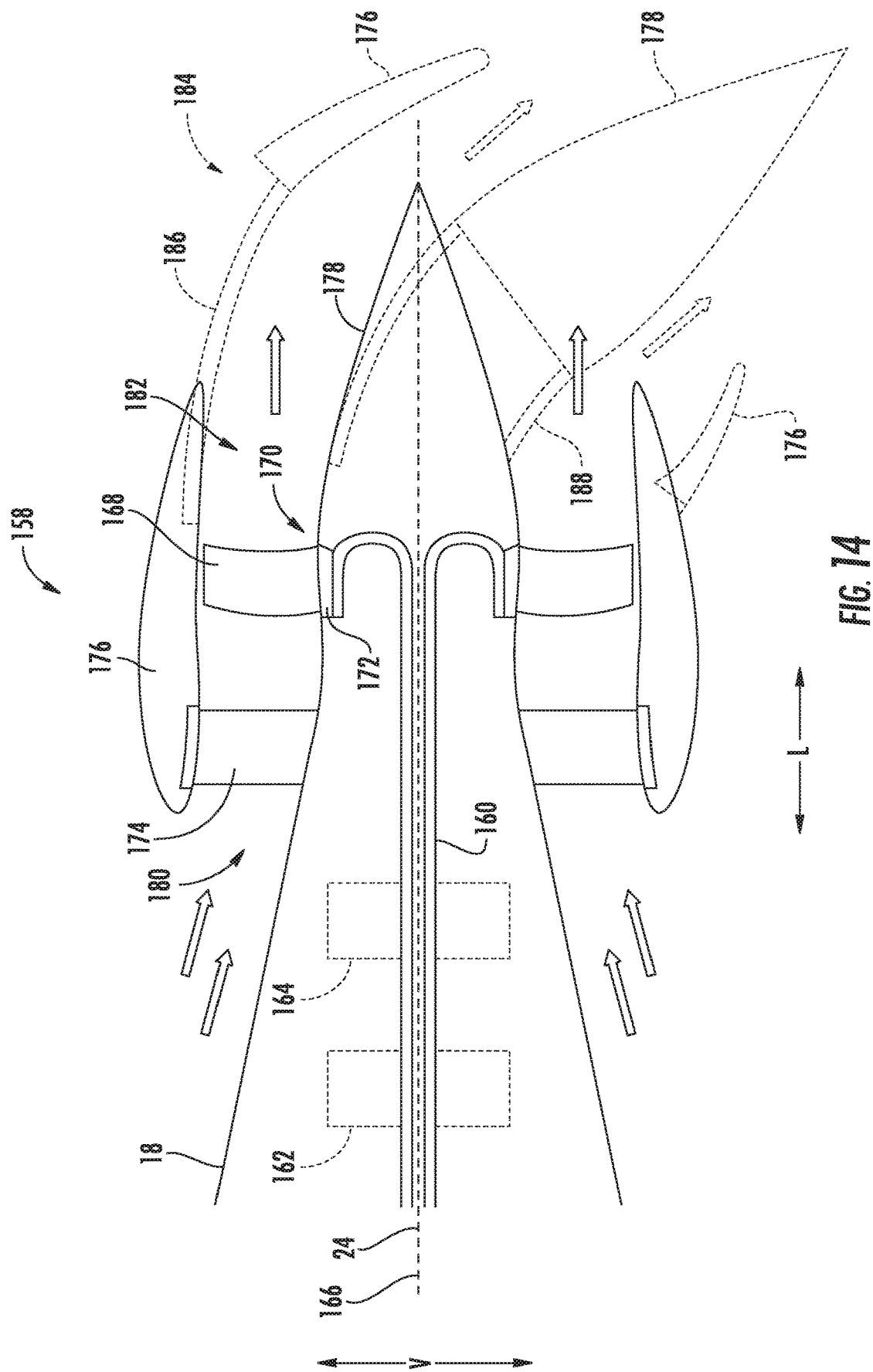
FIG. 14 is a side, schematic view of a supplemental propulsor as may be incorporated in the exemplary aircraft of FIG. 13.

Referring now also to FIG. 14, a side, cross-sectional view is provided of the aft fan 158 of the exemplary propulsion system 38 of FIG. 13. The aft fan 158 defines a centerline axis 166 that, for the embodiment depicted, aligns with the longitudinal centerline 12 of the aircraft 10, and further aligns with a mean line 24 of the aircraft 10. As shown, the exemplary aft fan 158 generally includes a plurality of fan blades 168 rotatable about the centerline axis 166 by the fan shaft 160. Specifically, each of the plurality of fan blades 168 are attached at a base 170 to a hub 172, the hub 172 coupled with the shaft 160.

The aft fan 158 additionally includes a plurality of forward support members 174, or struts, an outer nacelle 176, and a tail cone 178. The plurality of forward support members 174 are spaced along a circumferential direction C (i.e., a direction extending about the centerline axis 166; not shown) and extend between the fuselage 18 and the outer nacelle 176. The outer nacelle 176 extends substantially three hundred and sixty degrees (360°) around the mean line 24 of the aircraft 10, and the centerline axis 166 of the aft fan 158. Accordingly, the aft fan 158 also defines an inlet 180 at a forward end that also extends substantially 360° around the mean line 24 of the aircraft 10 and around the centerline axis 166 of the aft fan 158. Notably, the forward support members 174 may act as inlet guide vanes for the aft fan 158. Additionally, in certain embodiments, the aft fan 158 may additionally, or alternatively, include aft support members positioned aft of the plurality of fan blades 76 extending between the outer nacelle 176 and the tail cone 178.

During operation of the aft fan 158, the aft fan 158 is configured to ingest a flow of boundary layer air flowing over an outer surface of fuselage 18. The aft fan 158 receives the boundary layer air through the inlet 180 and re-energizes such flow of air through rotation of the plurality of fan blades 168. Notably, as discussed above, the plurality of fan blades 168 are rotatable by the turboshaft engine 124 of the propulsion system 38 through the fan shaft 160. The re-energized flow of air exits through a nozzle 182 defined between the outer nacelle 176 and the tail cone 178. The re-energized air may generate thrust through the nozzle 182, or alternatively, the re-energized air may simply reduce an amount of drag on the aircraft 10.

Moreover, referring still to FIG. 14, the aft fan 158 of the exemplary propulsion system 38 depicted may further include a thrust augmenter 184 movable between a forward thrust position and a vertical thrust position (depicted in phantom in the vertical thrust position). The thrust augmenter 184 may, when in the vertical thrust position, be configured to redirect the airflow through the nozzle 182 of the aft fan 158 such that the aft fan 158 generates substantially vertical thrust. For the embodiment depicted, the thrust augmenter 184 includes a plurality of nacelle extensions 186, which may be embedded within the outer nacelle 176 when in a forward thrust position, for extending and pivoting an aft portion of the outer nacelle 176. Additionally, the thrust augmenter 184 includes a plurality of tail cone extensions 188, for extending and pivoting the tail cone 178. However, in other embodiments, the thrust augmenter 184 may be configured in any other suitable manner.

Figure 15:
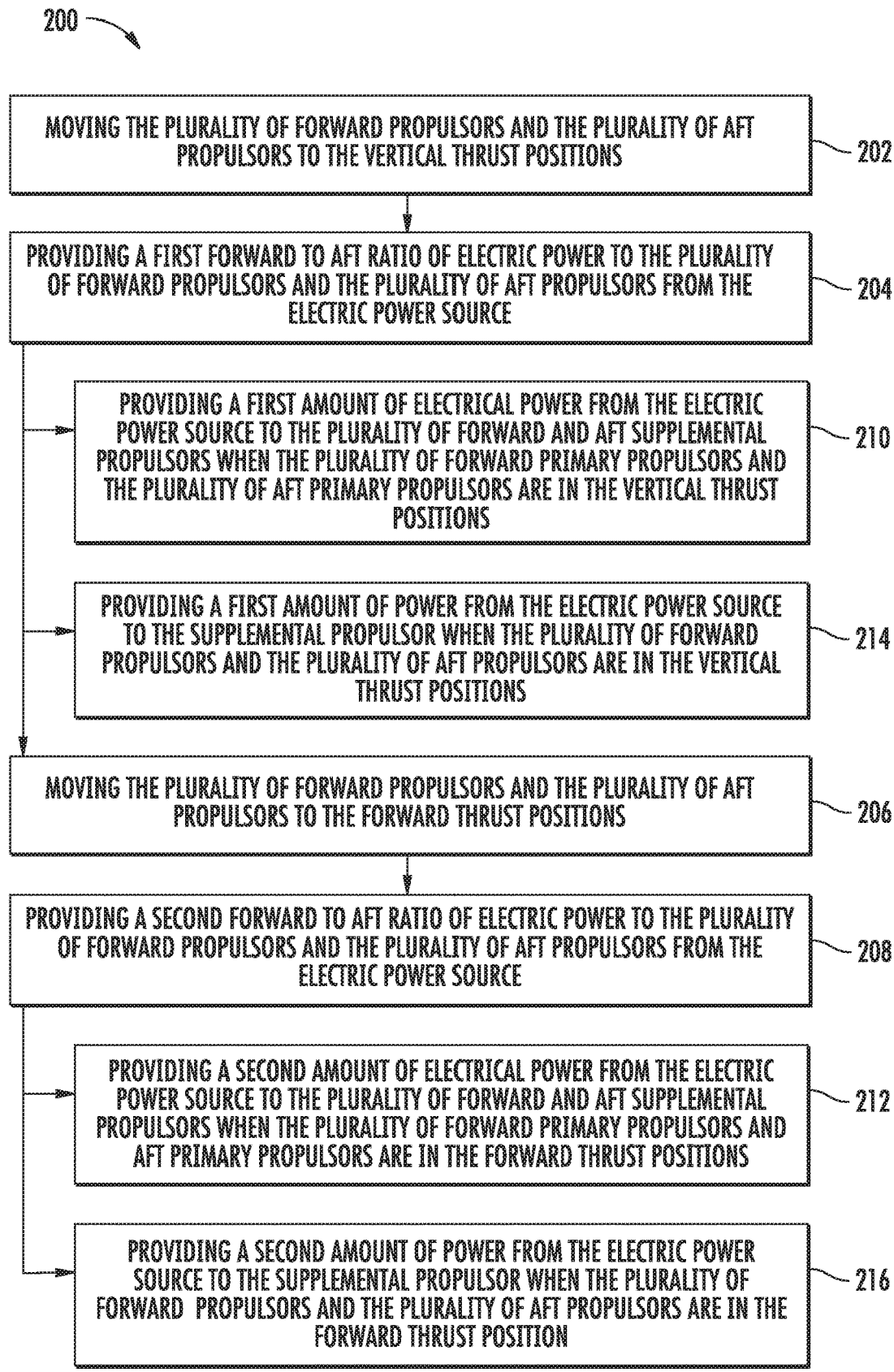
FIG. 15 is a flow diagram of a method for operating a propulsion system of the gas turbine engine in accordance with an exemplary aspect of the present disclosure.

Referring now to FIG. 15, the exemplary method (200) of operating a propulsion system of an aircraft in accordance with an exemplary aspect of the present disclosure is provided. The method (200) of FIG. 15 may be utilized with one or more of the exemplary propulsion systems and aircraft described above with reference to FIGS. 1 through 14. Accordingly, the propulsion system may include a plurality of forward propulsors and a plurality of aft propulsors, each powered by an electric power source and rotatable between a forward thrust position and a vertical thrust position.

As is depicted, the exemplary method (200) includes at (202) moving the plurality of forward propulsors and the plurality of aft propulsors to the vertical thrust positions. Additionally, the exemplary method (200) includes at (204) providing a first forward to aft ratio of electric power to the plurality of forward propulsors and the plurality of aft propulsors from the electric power source, such that the plurality of forward propulsors and the plurality of aft propulsors each generate vertical thrust. Providing the first forward to aft ratio of electric power at (204) may include providing the first forward to aft ratio of electric power during one or more of a takeoff operating mode, a hovering operating mode, or a landing operating mode.

Additionally, the exemplary method (200) includes at (206) moving the plurality of forward propulsors and the plurality of aft propulsors to the forward thrust positions. Once in the forward thrust positions, the exemplary method (200) includes at (208) providing a second forward to aft ratio of electric power to the plurality of forward propulsors and the plurality of aft propulsors from the electric power source, such that one or more of the plurality of forward propulsors and the plurality of aft propulsors generate a forward thrust.

Notably, for the exemplary method (200), the first forward to aft ratio of electric power is different than the second forward to aft ratio of electric power. For example, in certain aspects, the first forward to aft ratio of electric power is greater than the second forward to aft ratio of electric power. Alternatively, however, in other aspects, the second forward to aft ratio of electric power is greater than the first forward to aft ratio of electric power. Such an exemplary aspect allow for the propulsion system to include certain propulsors configured for use during, e.g., vertical thrust operations, such as takeoff, hovering, and landing operations, while other propulsors are additionally configured for use during, e.g., cruise operations.

As will be appreciated, from the above description, in certain aspects, the plurality of forward propulsors may be configured as a plurality of forward primary propulsors and the propulsion system may further include a plurality of forward supplemental propulsors. Similarly, the plurality of aft propulsors may be configured as a plurality of aft primary propulsors and the propulsion system may further include a plurality of aft supplemental propulsors. With such an exemplary embodiment, the exemplary method (200) may additionally include at (210) providing a first amount of electrical power from the electric power source to the plurality of forward and aft supplemental propulsors when the plurality of forward primary propulsors and the plurality of aft primary propulsors are in the vertical thrust positions. The method may additionally include at (212) providing a second amount of electrical power from the electric power source to the plurality of forward and aft supplemental propulsors when the plurality of forward primary propulsors and aft primary propulsors are in the forward thrust positions. For the exemplary aspect depicted, the second amount of electrical power is greater than the first amount of electrical power. For example, in certain exemplary aspects, the first amount of electrical power may be less than about half of the second amount of electrical power. With such an exemplary aspect, the primary propulsors may be most suitable for vertical thrust operations, and the supplemental propulsors may be most suitable for forward thrust operations. Specifically, with such an exemplary aspect, the primary propulsors may be used for, e.g., takeoff, hovering, and landing operations, while the supplemental propulsors may be used for, e.g., cruise operations.

Referring still to the exemplary aspect of FIG. 15, the exemplary method (200) may further apply to a propulsion system for an aircraft further including a supplemental propulsor mounted to a fuselage of the aircraft. The supplemental propulsor may be mounted at an aft end of the fuselage, and may further be configured to ingest and re-energize a boundary layer air flowing over the fuselage of the aircraft. Accordingly, in certain exemplary aspects, the supplemental propulsor may be a boundary layer ingestion aft fan. With such an exemplary aspect, the exemplary method (200) further includes at (214) providing a first amount of power from the electric power source to the supplemental propulsor when the plurality of forward propulsors and the plurality of aft propulsors are in the vertical thrust positions. The exemplary method (200) further includes at (216) providing a second amount of power from the electric power source to the supplemental propulsor when the plurality of forward propulsors and the plurality of aft propulsors are in the forward thrust position. For the exemplary aspect depicted, the second amount of power is greater than the first amount of power. For example, the first amount of power may be less than about half of the second amount of power. Accordingly, for the aspect depicted, the supplemental propulsor may be generally be configured for use during forward flight operations, such as during cruise operations.

Additionally or alternatively, however, the propulsion system may further include a thrust augmenter configured with the supplemental propulsor. With such an embodiment, the method (200) may include moving the thrust augmenter to a vertical thrust position when the primary propulsors are in the vertical thrust positions, and moving the thrust augmenter to a forward thrust position when the primary propulsors are in the forward thrust positions. Alternatively still, the method (200) may instead include moving the supplemental propulsor between a vertical thrust position and a forward thrust position.

Figure 16:
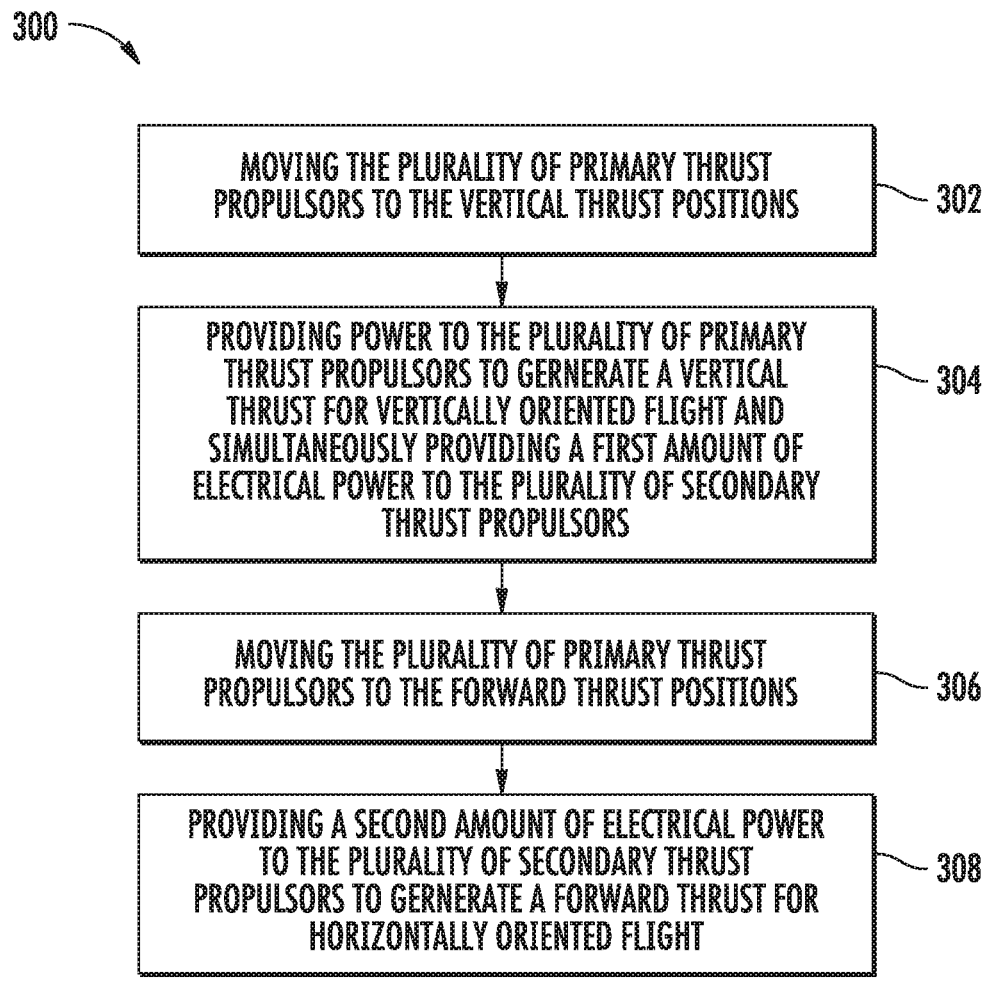
FIG. 16 is a flow diagram of a method for operating a propulsion system of the gas turbine engine in accordance with another exemplary aspect of the present disclosure.

Referring now to FIG. 16, providing a flow diagram of a method (300) in accordance with another exemplary aspect of the present disclosure, the method (300) may be utilized with a propulsion system in accordance with one or more of the above embodiments including a plurality of primary thrust propulsors and a plurality of secondary thrust propulsors.

The method (300) includes at (302) moving the plurality of primary thrust propulsors to the vertical thrust positions. In certain exemplary aspects, moving the plurality of primary thrust propulsors at (302) to the vertical thrust positions may further include moving the plurality of secondary thrust propulsors to the vertical thrust positions. The method (300) further includes at (304) providing power to the plurality of primary thrust propulsors to generate a vertical thrust for vertically oriented flight and simultaneously providing a first amount of electrical power to the plurality of secondary thrust propulsors.

The exemplary method (300) further includes at (306) moving the plurality of primary thrust propulsors to the forward thrust positions. Again, in certain exemplary aspects, moving the plurality of primary thrust propulsors at (306) to the forward thrust positions may include moving the plurality of secondary thrust propulsors to the forward thrust positions. The method (300) next includes at (308) providing a second amount of electrical power to the plurality of secondary thrust propulsors to generate a forward thrust for horizontally oriented flight. For the exemplary aspect depicted, the second amount of electrical power is greater than the first amount of electrical power, such that the plurality secondary thrust propulsors generate more thrust in the forward flight positions and during forward flight than when in the vertical thrust positions and during vertically oriented flight.

In certain exemplary aspects, the second amount of electrical power is at least about two times greater than the first amount of electrical power, such as at least about four times greater than the first amount of electrical power. Moreover, in certain exemplary aspects, the first amount of electrical power may be less than 10% of the second amount of electrical power. Moreover, the aircraft with which the propulsion system is configured may define a minimum necessary takeoff thrust. With such an exemplary aspect, providing power to the plurality primary thrust propulsors to generate vertical thrust at (304) may include providing power to the plurality of primary thrust propulsors to generate a vertical thrust within at least about 10% of the minimum necessary takeoff thrust.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. A propulsion system of an aircraft comprising:
 a plurality of forward propulsors;
 a plurality of aft propulsors, each powered by an electric power source and rotatable between a forward thrust position and a vertical thrust position; and
 a controller,
 wherein the plurality of forward propulsors and the plurality of aft propulsors are configured to move to the vertical thrust positions,
 wherein the controller is configured to provide a first forward to aft ratio of electric power to the plurality of forward propulsors and the plurality of aft propulsors from the electric power source, such that the plurality of forward propulsors and plurality of aft propulsors each generate vertical thrust,
 wherein the plurality of forward propulsors and the plurality of aft propulsors are configured to move to the forward thrust positions,
 wherein the controller is configured to provide a second forward to aft ratio of electric power to the plurality of forward propulsors and the plurality of aft propulsors from the electric power source, and
 wherein the first forward to aft ratio of electric power is different than the second forward to aft ratio of electric power.

2. The propulsion system of claim 1, wherein the first forward to aft ratio of electric power is greater than the second forward to aft ratio of electric power.

3. The propulsion system of claim 2, wherein the second forward to aft ratio of electric power is less than ten percent (10%) of the first forward to aft ratio of electric power.

4. The propulsion system of claim 1, wherein the second forward to aft ratio of electric power is greater than the first forward to aft ratio of electric power.

5. The propulsion system of claim 4, wherein the first forward to aft ratio of electric power is less than ten percent (10%) of the second forward to aft ratio of electric power.

6. The propulsion system of claim 1,
wherein the propulsion system further comprises a supplemental propulsor, and
wherein the controller is further configured to:
a first amount of power from the electric power source to the supplemental propulsor when the plurality of forward propulsors and plurality of aft propulsors are in the vertical thrust positions; and
provide a second amount of power from the electric power source to the supplemental propulsor when the plurality of forward propulsors and the plurality of aft propulsors are in the forward thrust positions, and
wherein the second amount of power is greater than the first amount of power.

7. The propulsion system of claim 6, wherein the supplemental propulsor is a fan mounted to the fuselage of the aircraft.

8. The propulsion system of claim 6, wherein the first amount of power is less than about half of the second amount of power.

9. The propulsion system of claim 1,
wherein the electric power source comprises a combustion engine and an electric generator, and
wherein the combustion engine drives the electric generator.

10. The propulsion system of claim 1, wherein the electric power source is located remotely from the plurality of forward propulsors and the plurality of aft propulsors.

11. The propulsion system of claim 1,
wherein the plurality of forward propulsors are configured as a plurality of forward primary thrust propulsors,
wherein the plurality of aft propulsors are configured as a plurality of aft primary thrust propulsors,
wherein the propulsion system further comprises a plurality of forward secondary thrust propulsors and a plurality of aft secondary thrust propulsors, and
wherein the controller is further configured to:
provide a first amount of electrical power from the electric power source to the plurality of forward and aft secondary thrust propulsors when the plurality of forward and aft primary thrust propulsors are in the vertical thrust positions, and
provide a second amount of electrical power from the electric power source to the plurality of forward and aft secondary thrust propulsors when the plurality of forward and aft primary thrust propulsors are in the forward thrust positions,
wherein the second amount of electrical power is greater than the first amount of electrical power.

12. The propulsion system of claim 11, wherein the first amount of electrical power is less than about half of the second amount of electrical power.

13. A propulsion system of an aircraft comprising:
a plurality of primary thrust propulsors;
a plurality of secondary thrust propulsors, each powered by an electric power source and rotatable between a forward thrust position and a vertical thrust position; and
a controller,
wherein the plurality of primary thrust propulsors are configured to move to the vertical thrust positions,
wherein the controller is configured to provide power to the plurality of primary thrust propulsors to generate a vertical thrust for vertically oriented flight and simultaneously providing a first amount of electrical power to the plurality of secondary thrust propulsors,
wherein the plurality of primary thrust propulsors are configured to move to the forward thrust positions, and
wherein the controller is configured to provide a second amount of electrical power to the plurality of secondary thrust propulsors to generate a forward thrust for horizontally oriented flight, and
wherein the second amount of electrical power is greater than the first amount of electrical power.

14. The propulsion system of claim 13, wherein the second amount of electrical power is at least about two times greater than the first amount of electrical power.

15. The propulsion system of claim 13, wherein the second amount of electrical power is at least about four times greater than the first amount of electrical power.

16. The propulsion system of claim 13, wherein the first amount of electrical power is less than ten percent of the second amount of electrical power.

17. The propulsion system of claim 13,
wherein the aircraft defines a minimum necessary takeoff thrust, and
wherein the controller is configured to provide power to the plurality of primary thrust propulsors to generate a vertical thrust within ten percent of the minimum necessary takeoff thrust.

18. The propulsion system of claim 13,
wherein the plurality of primary thrust propulsors comprises a plurality of forward primary thrust propulsors and a plurality of aft primary thrust propulsors,
wherein the controller is configured to provide a first forward to aft ratio of electric power to the plurality of forward and aft propulsors, and
wherein the controller is further configured to provide a second forward to aft ratio of electric power to the plurality of forward propulsors and the plurality of aft propulsors from the electric power source, and
wherein the first forward to aft ratio of electric power is different than the second forward to aft ratio of electric power.

19. The propulsion system of claim 13,
wherein the plurality of primary thrust propulsors and the plurality of secondary thrust propulsors are configured to move to the vertical thrust positions, and
wherein the plurality of primary thrust propulsors and the plurality of secondary thrust propulsors are configured to move to the forward thrust positions.

20. The propulsion system of claim 13, wherein the electric power source comprises a combustion engine configured to generate at least about 1,500 horsepower and an electric generator driven by the combustion engine and configured to generate at least about 1.12 megawatts.

* * * * *